US012343324B2

(12) United States Patent
Prud'Homme et al.

(10) Patent No.: US 12,343,324 B2
(45) Date of Patent: *Jul. 1, 2025

(54) DIHYDROMYRICETIN HOT MELT EXTRUSION FORMULATIONS AND METHODS FOR FORMING THEM

(71) Applicants: The Trustees of Princeton University, Princeton, NJ (US); Cheers Health, Inc., Houston, TX (US)

(72) Inventors: Robert K. Prud'Homme, Princeton, NJ (US); Brooks Powell, Houston, TX (US); Vikram Pansare, Princeton, NJ (US); Nicholas Caggiano, Princeton, NJ (US)

(73) Assignees: The Trustees of Princeton University, Princeton, NJ (US); Cheers Health, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/943,691

(22) Filed: Sep. 13, 2022

(65) Prior Publication Data

US 2023/0285352 A1    Sep. 14, 2023

Related U.S. Application Data

(63) Continuation of application No. 16/683,387, filed on Nov. 14, 2019, now abandoned.

(60) Provisional application No. 62/767,208, filed on Nov. 14, 2018.

(51) Int. Cl.
| | |
|---|---|
| *A61K 31/352* | (2006.01) |
| *A61K 9/06* | (2006.01) |
| *A61K 9/10* | (2006.01) |
| *A61K 9/16* | (2006.01) |
| *A61K 9/28* | (2006.01) |
| *A61K 45/06* | (2006.01) |

(52) U.S. Cl.
CPC .............. *A61K 31/352* (2013.01); *A61K 9/06* (2013.01); *A61K 9/10* (2013.01); *A61K 9/1617* (2013.01); *A61K 9/1647* (2013.01); *A61K 9/2846* (2013.01); *A61K 45/06* (2013.01)

(58) Field of Classification Search
CPC .... A61K 9/146; A61K 9/1629; A61K 9/1635; A61K 9/1641; A61K 31/352; A61K 31/353
See application file for complete search history.

(56) References Cited

U.S. PATENT DOCUMENTS

| | | |
|---|---|---|
| 1,690,760 A | 11/1928 | Volwiler |
| 3,239,370 A | 3/1966 | Thomson et al. |
| 3,410,938 A | 11/1968 | Schippers |
| 4,678,516 A | 7/1987 | Alderman et al. |
| 4,695,464 A | 9/1987 | Alderman |
| 5,152,923 A | 10/1992 | Weder et al. |
| 5,851,579 A | 12/1998 | Wu et al. |
| 6,274,150 B1 | 8/2001 | Simonnet et al. |
| 6,291,013 B1 | 9/2001 | Gibson et al. |
| 6,335,022 B1 | 1/2002 | Simon net et al. |
| 6,375,960 B1 | 4/2002 | Simonnet et al. |
| 6,413,527 B1 | 7/2002 | Simonnet et al. |
| 6,488,963 B1 | 12/2002 | McGinity et al. |
| 6,610,653 B1 | 8/2003 | Backstrom et al. |
| 6,689,371 B1 | 2/2004 | Simonnet et al. |
| 6,730,322 B1 | 5/2004 | Bernstein et al. |
| 6,763,607 B2 | 7/2004 | Beyerinck et al. |
| 6,902,737 B2 | 6/2005 | Quemin |
| 6,998,426 B2 | 2/2006 | L'Alloret et al. |
| 7,052,719 B2 | 5/2006 | Bernstein et al. |
| 7,842,308 B2 | 11/2010 | McAllister et al. |
| 7,977,024 B2 | 7/2011 | Zhou et al. |
| 8,137,699 B2 | 3/2012 | Johnson et al. |
| 8,298,581 B2 | 10/2012 | Fischer et al. |
| 8,486,423 B2 | 7/2013 | Brough et al. |
| 8,603,514 B2 | 12/2013 | Yang et al. |
| 8,623,329 B1 | 1/2014 | Hansen et al. |
| 8,703,196 B2 | 4/2014 | Babcock et al. |
| 9,504,658 B2 | 11/2016 | Miller et al. |
| 9,603,830 B2 | 3/2017 | Powell |
| 10,231,937 B2 | 3/2019 | Pagels et al. |
| 10,786,522 B2 | 9/2020 | Burgos et al. |
| 11,103,461 B2 | 8/2021 | Prud'Homme et al. |
| 2001/0044474 A1 | 11/2001 | Curatolo et al. |
| 2003/0049311 A1 | 3/2003 | McAllister et al. |
| 2003/0054037 A1 | 3/2003 | Babcock et al. |
| 2003/0104063 A1 | 6/2003 | Babcock et al. |
| 2003/0163931 A1 | 9/2003 | Beyerinck et al. |

(Continued)

FOREIGN PATENT DOCUMENTS

| | | |
|---|---|---|
| CA | 1236009 | 5/1988 |
| CN | 1293825 C | 1/2007 |

(Continued)

OTHER PUBLICATIONS

Ruan et al., "Improving the solubility of ampelopsin by solid dispersions and inclusion complexes", 2005, Journal of Pharmaceutical and Biomedical Analysis, vol. 38, pp. 457-464. (Year: 2005).*

Prudic et al., "Influence of Copolymer Composition on the Phase Behavior of Solid Dispersions", 2014, Molecular Pharmaceutics, vol. 11, pp. 4189-4198. (Year: 2014).*

English machine translation of CN-108524493-A made Jul. 9, 2021. (Year: 2021).*

Yu et al., "Evidence-based prevention of Alzheimer's disease: systematic review and meta-analysis of 243 observational prospective studies and 153 randomized controlled trials", Jul. 20, 2020, Journal of Neurology, Neurosurgery & Psychiatry, vol. 91, Issue 11, pp. 1201-1209. (Year: 2020).*

(Continued)

*Primary Examiner* — Michael B. Pallay
(74) *Attorney, Agent, or Firm* — Nixon & Vanderhye P.C.; Lars H. Genieser

(57) ABSTRACT

Compositions including dihydromyricetin (DHM) and methods for forming them through hot melt extrusion.

25 Claims, No Drawings

(56) References Cited

U.S. PATENT DOCUMENTS

| | | |
|---|---|---|
| 2003/0170309 A1 | 9/2003 | Babcock et al. |
| 2003/0185893 A1 | 10/2003 | Beyerinck et al. |
| 2003/0228358 A1* | 12/2003 | Perlman .............. A61K 31/496 |
| | | 424/465 |
| 2004/0052824 A1 | 3/2004 | Chacra-Vernet et al. |
| 2004/0091546 A1 | 5/2004 | Johnson et al. |
| 2004/0115256 A1 | 6/2004 | MacAllister et al. |
| 2004/0132771 A1 | 7/2004 | Babcock et al. |
| 2004/0156905 A1 | 8/2004 | Babcock et al. |
| 2004/0185112 A1 | 9/2004 | Beyerinck et al. |
| 2004/0194338 A1 | 10/2004 | Beyerinck et al. |
| 2006/0040831 A1 | 2/2006 | Cassidy et al. |
| 2006/0057215 A1 | 3/2006 | Raiche et al. |
| 2006/0224095 A1 | 10/2006 | Claverie et al. |
| 2007/0231355 A1 | 10/2007 | Quadir et al. |
| 2007/0281003 A1 | 12/2007 | Fuisz et al. |
| 2008/0145432 A1 | 6/2008 | Kakizawa et al. |
| 2008/0274194 A1 | 11/2008 | Miller et al. |
| 2009/0053315 A1 | 2/2009 | Brough et al. |
| 2009/0155326 A1 | 6/2009 | Mack et al. |
| 2010/0166866 A1 | 7/2010 | Fischer et al. |
| 2010/0305219 A1 | 12/2010 | Granick et al. |
| 2010/0330368 A1 | 12/2010 | Prud'homme et al. |
| 2011/0022129 A1 | 1/2011 | Prud'homme et al. |
| 2011/0064821 A1 | 3/2011 | Catchpole et al. |
| 2011/0206739 A1 | 8/2011 | Nicolosi et al. |
| 2011/0229516 A1 | 9/2011 | Ochomogo et al. |
| 2012/0009267 A1 | 1/2012 | Cho et al. |
| 2012/0121510 A1 | 5/2012 | Brem et al. |
| 2012/0171254 A1 | 7/2012 | Johnson et al. |
| 2013/0053435 A1 | 2/2013 | Liang et al. |
| 2013/0064954 A1 | 3/2013 | Ochomogo et al. |
| 2013/0337078 A1 | 12/2013 | Mayer et al. |
| 2013/0337096 A1* | 12/2013 | Purcell ................ A61K 38/17 |
| | | 424/773 |
| 2014/0099379 A1 | 4/2014 | Beck-Broichsitter et al. |
| 2014/0249235 A1 | 9/2014 | Brugel et al. |
| 2014/0302154 A1 | 10/2014 | Waldoefner et al. |
| 2014/0356443 A1 | 12/2014 | Brisander et al. |
| 2015/0218198 A1 | 8/2015 | Petermann et al. |
| 2015/0290233 A1 | 10/2015 | Yarden et al. |
| 2015/0298084 A1 | 10/2015 | Schoeppe et al. |
| 2015/0342923 A1 | 12/2015 | Powell |
| 2016/0051484 A1 | 2/2016 | Kataoka et al. |
| 2016/0235677 A1 | 8/2016 | Hoerr et al. |
| 2016/0317459 A1 | 11/2016 | Ensign et al. |
| 2016/0346266 A1 | 12/2016 | Tolleth et al. |
| 2017/0042823 A1 | 2/2017 | Prud'homme et al. |
| 2017/0209386 A1 | 7/2017 | Pagels et al. |
| 2018/0125915 A1 | 5/2018 | Mikhail |
| 2019/0008788 A1 | 1/2019 | Prud'Homme et al. |
| 2019/0105293 A1 | 4/2019 | Howes et al. |
| 2019/0151252 A1 | 5/2019 | Pagels et al. |
| 2019/0192444 A1 | 6/2019 | Barzilay et al. |
| 2020/0023332 A1 | 1/2020 | Prud'homme et al. |
| 2020/0147032 A1 | 5/2020 | Prud'homme et al. |
| 2020/0206136 A1 | 7/2020 | Prud'homme et al. |
| 2020/0215027 A1 | 7/2020 | Prud'homme et al. |
| 2022/0062223 A1 | 3/2022 | Prud'homme et al. |
| 2023/0172949 A1 | 6/2023 | Brough et al. |
| 2023/0210812 A1 | 7/2023 | Prud'homme et al. |
| 2023/0285352 A1 | 9/2023 | Prud'Homme et al. |
| 2024/0261254 A1 | 8/2024 | Prud'homme et al. |
| 2024/0408050 A1 | 12/2024 | Prud'homme et al. |

FOREIGN PATENT DOCUMENTS

| | | | |
|---|---|---|---|
| CN | 100389766 C | 5/2008 | |
| CN | 102048160 A | 5/2011 | |
| CN | 102058560 A | 5/2011 | |
| CN | 102334609 A | 2/2012 | |
| CN | 104042567 A | 9/2014 | |
| CN | 104666293 A | 6/2015 | |
| CN | 105213250 A | 1/2016 | |
| CN | 105796512 A | 7/2016 | |
| CN | 106750272 A | 5/2017 | |
| CN | 107334729 A | 11/2017 | |
| CN | 107536830 A | 1/2018 | |
| CN | 108524493 A * | 9/2018 | ........... A61K 31/352 |
| EP | 4008314 A2 | 6/2022 | |
| JP | 2015-129128 | 7/2015 | |
| WO | 1994008599 A1 | 4/1994 | |
| WO | WO 1994/008610 A1 | 4/1994 | |
| WO | 1997049736 A2 | 12/1997 | |
| WO | WO 1999/056727 A2 | 11/1999 | |
| WO | 2002076441 A1 | 10/2002 | |
| WO | 2002078674 A1 | 10/2002 | |
| WO | WO 2002/092069 A1 | 11/2002 | |
| WO | WO 2009/067734 A1 | 6/2009 | |
| WO | 2009080164 A1 | 7/2009 | |
| WO | 2013023003 A1 | 2/2013 | |
| WO | WO 2014/140991 A1 | 9/2014 | |
| WO | 2015130835 A1 | 9/2015 | |
| WO | WO 2015/140138 A1 | 9/2015 | |
| WO | 2015200054 A2 | 12/2015 | |
| WO | 2015200054 A9 | 12/2015 | |
| WO | 2016193810 A1 | 12/2016 | |
| WO | 2017089942 | 6/2017 | |
| WO | 2017112828 A1 | 6/2017 | |
| WO | WO 2017/130046 A1 | 8/2017 | |
| WO | 2019055539 A1 | 3/2019 | |
| WO | WO 2019/050969 A1 | 3/2019 | |
| WO | 2019090030 A1 | 5/2019 | |
| WO | 2020018890 A1 | 1/2020 | |
| WO | WO 2020/099937 A2 | 5/2020 | |
| WO | 2020227350 A1 | 11/2020 | |
| WO | WO 2020252346 A1 | 12/2020 | |
| WO | 2021046078 A1 | 3/2021 | |

OTHER PUBLICATIONS

Loomans-Kropp et al., "Cancer prevention and screening: the next step in the era of precision medicine", Jan. 28, 2019, npj Precision Oncology, vol. 3, No. 3, pp. 1-8. (Year: 2019).*

Naveed et al., "Pharmacological Primary Prevention of Diabetes Mellitus Type II: A Narrative Review", Aug. 25, 2020, Cureus, vol. 12, No. 8, pp. 1-14. (Year: 2020).*

Aungst, B.J., "Absorption Enhancers: Applications and Advances", AAPS J., (2012) vol. 14, No. 1, pp. 10-18.

Anton, N. et al., "Nano-emulsions and nanocapsules by the PIT method: an investigation on the role of the temperature cycling on the emulsion phase inversion", Int'l J. Pharmaceutics, (2007) vol. 344, Nos. 1-2, pp. 44-52.

Anton, N. & Vandamme, T.F., "The universality of low-energy nano-emulsification", Int'l J. Pharmaceutics, (2009) vol. 377, Nos. 1-2, pp. 142-147.

Babu, N.J. & Nangia, A, "Solubility Advantage of Amorphous Drugs and Pharmaceutical Cocrystals", Crystal Growth & Design, (2011) vol. 11, pp. 2662-2679.

Bailly, N. et al. "Poly(N-vinylpyrrolidone)-block-poly(vinyl acetate) as a Drug Delivery Vehicle for Hydrophobic Drugs", Biomacromolecules, (2012) vol. 13, pp. 4109-4117.

BASF, Luviscol VA Grades Technical Information, Jun. 2012, pp. 1-14.

Bouchemal, K. et al., "Nano-emulsion formulation using spontaneous emulsification: solvent, oil and surfactant optimization", Int'l J. Pharmaceutics, (2004) vol. 280, Nos. 1-2, pp. 241-251.

Breitenbach, J., "Melt extrusion: from process to drug delivery technology", European J. Pharmaceutics & Biopharmaceutics, (2002) vol. 54, No. 2, pp. 107-117.

Chokshi, R. & Zia, H., "Hot-Melt Extrusion Technique: A Review", Iranian J. Pharmaceutical Research, (2004) vol. 3, pp. 3-16.

"The Complete Guide to Enteric Coating", https://astenzymes.com/the-complete-guide-to-enteric-coating/, accessed Aug. 11, 2020, pp. 1-11.

Crowley, M.M., et al., "Pharmaceutical applications of hot-melt extrusion: part I", Drug Development & Industrial Pharmacy, (2007) vol. 33, No. 9, pp. 909-926.

(56) References Cited

OTHER PUBLICATIONS

D'Addio, S.M. & Prud'homme, R.K., "Controlling drug nanoparticle formation by rapid precipitation", Advanced Drug Delivery Reviews, (2011) vol. 63, No. 6, pp. 417-426.
Davies, D.L. et al., "Recent Advances in the Discovery and Preclinical Testing of Novel Compounds for the Prevention and/or Treatment of Alcohol Use Disorders", Alcoholism: Clinical & Experimental Research, (2013) vol. 37, No. 1, pp. 8-15.
"Enteric Coating—The Enteric Coating Process", https://www.xtend-life.com/pages/enteric-coating, accessed Aug. 12, 2020, pp. 1-6.
Etchenausia, L. et al., "RAFT/MADIX emulsion copolymerization of vinyl acetate and N-vinylcaprolactam: towards waterborne physically crosslinked thermoresponsive particles", Polymer Chemistry, (2017) DOI: 10.1039/C7PY00221A, pp. 1-28.
Fang, H.-L. et al., "Treatment of Chronic Liver Injuries in Mice by Oral Administration of Ethanolic Extract of the Fruit of Hovenia dulcis", American J. of Chinese Medicine, (2007), vol. 35, No. 4, pp. 693-703.
Ganachaud, F. & Katz, J.L., "Nanoparticles and Nanocapsules Created Using the Ouzo Effect: Spontaneous Emulsification as an Alternative to Ultrasonic and High-Shear Devices", ChemPhysChem, (2005) vol. 6, No. 2, pp. 209-216.
Guo, Q. et al., "Binding of dihydromyricetin and its metal ion complexes with bovine serum albumin", Biotechnology & Biotechnological Equipment, (2014) vol. 28, No. 2, pp. 333-341.
Guo, Q. et al., "Biosynthesis of gold nanoparticles using a kind of flavanol: Dihydromyricetin", Colloids & Surfaces A: Physicochem. & Engineering Aspects, (2014) vol. 441, pp. 127-132.
Guo, Q. et al., "Synthesis of dihydromyricetin-manganese (II) complex and interaction with DNA", J. Molecular Structure, (2012) vol. 1027, pp. 64-69.
Gupta, A et al., "Nanoemulsions: formation, properties and applications", Soft Matter, (2016) vol. 12, No. 11, pp. 2826-2841.
Hase, K. et al., "Hepatoprotective Effect of Hovenia dulcis THUNB. on Experimental Liver Injuries Induced by Carbon Tetrachloride or D-Galactosamine/Lipopolysaccharide", Biol. Pharm. Bull., (1997) vol. 20, No. 4, pp. 381-385.
Hu, J. et al., "Nanoparticle Engineering Processes for Enhancing the Dissolution Rates of Poorly Water Soluble Drugs", Drug Development & Industrial Pharmacy, (2004) vol. 30, No. 3, pp. 233-245.
International Patent Application PCT/US2018/049580 International Search Report dated Jan. 15, 2019.
International Patent Application PCT/US2018/049580 Written Opinion dated Jan. 15, 2019.
International Patent Application PCT/IB2019/001381 International Search Report dated Jun. 23, 2020.
International Patent Application PCT/IB2019/001381 Written Opinion dated Jun. 23, 2020.
International Patent Application PCT/US2020/037542 International Search Report dated Sep. 11, 2020.
International Patent Application PCT/US2020/037542 Written Opinion dated Sep. 11, 2020.
Izquierdo, P. et al., "Formation and Stability of Nano-Emulsions Prepared Using the Phase Inversion Temperature Method", Langmuir, (2002) vol. 18, No. 1, pp. 26-30.
Jain, M.S. et al., "Spray Drying in Pharmaceutical Industry: A Review", Research J. Pharma. Dosage Forms & Tech., (2011), vol. 4, No. 2, pp. 74-79.
Kelmann, R.G. et al., "Carbamazepine parenteral nanoemulsions prepared by spontaneous emulsification process", Int'l J. Pharmaceutics, (2007) vol. 342, Nos. 1-2, pp. 231-239.
Li, H. et al., "The Versatile Effects of Dihydromyricetin in Health", Evidence Based Complementary & Alternative Medicine, (2017) Art. ID 1053617, pp. 1-10.
Liang, J. & Olsen, R.W., "Alcohol use disorders and current pharmacological therapies: the role of GABAA receptors", Acta Pharmacologica Sinica, (2014) vol. 35, No. 8, pp. 981-993.

Liang, J., et al., "Dihydromyricetin Prevents Fetal Alcohol Exposure-Induced Behavioral and Physiological Deficits: The Roles of GABAA Receptors in Adolescence", Neurochemical Research, (2014) vol. 39, No. 6, pp. 1147-1161.
Liu, Y. et al., "Mixing in a multi-inlet vortex mixer (MIVM) for flash nano-precipitation", Chemical Engineering Science, (2008), vol. 63, No. 11, pp. 2829-2842.
Maniruzzaman, M. et al., "A Review of Hot-Melt Extrusion: Process Technology to Pharmaceutical Products", ISRN Pharmaceutics, (2012) vol. 2012, Article ID 436763, pp. 1-9.
Murakami, H. et al., "Preparation of poly (DL-lactide-co-glycolide) nanoparticles by modified spontaneous emulsification solvent diffusion method", Int'l J. Pharmaceutics, (1999) vol. 187, No. 2, pp. 143-152.
Niwa, T. et al., "Preparations of biodegradable nanospheres of water-soluble and insoluble drugs with D, L-lactide/glycolide copolymer by a novel spontaneous emulsification solvent diffusion method, and the drug release behavior", J. Controlled Release, (1993) vol. 25, Nos. 1-2, pp. 89-98.
Okuma, Y. et al., "Effect of Extracts from Hovenia dulcis Thunb. on Alcohol Concentration in Rats and Men Administered Alcohol", J. Japan Society of Nutrition & Food Sciences, (1995), vol. 48, No. 3, pp. 167-172 (English-language abstract).
Onoue, S. et al., "Self-micellizing solid dispersion of cyclosporine A with improved dissolution and oral bioavailability", Eur. J. Pharm. Sci., (2014), vol. 62, pp. 16-22.
Patil, H. et al., "Hot-Melt Extrusion: from Theory to Application in Pharmaceutical Formulation", AAPS PharmSciTech, (2016) vol. 17, No. 1, pp. 20-42.
Prudic, A et al., "Influence of Copolymer Composition on the Phase Behavior of Solid Dispersions", Molecular Pharmaceutics, (2014) vol. 11, pp. 4189-4198.
Rang, M.-J. & Miller, C.A., "Spontaneous Emulsification of Oils Containing Hydrocarbon, Nonionic Surfactant, and Oleyl Alcohol", J. Colloid & Interface Science, (1999) vol. 209, No. 1, pp. 179-192.
Roger, K. et al., "Formation of 10-100 nm Size-Controlled Emulsions through a Sub-PIT Cycle", Langmuir, (2010) vol. 26, No. 6, pp. 3860-3867.
Roger, K. et al., "Emulsification through Surfactant Hydration: The PIC Process Revisited", Langmuir, (2011) vol. 27, No. 2, pp. 604-611.
Roger, K. et al., "Superswollen Microemulsions Stabilized by Shear and Trapped by a Temperature Quench", Langmuir, (2011) vol. 27, No. 17, pp. 10447-10454.
Ruan, L.-P. et al., "Improving the solubility of ampelopsin by solid dispersions and inclusion complexes", J. Pharmaceutical & Biomedical Analysis, (2005) vol. 38, pp. 457-464.
Ruschak, K.J. & Miller, C.A., "Spontaneous Emulsification in Ternary Systems with Mass Transfer", Industrial & Engineering Chemistry Fundamentals, (1972) vol. 11, No. 4, pp. 534-540.
Saad, W.S. & Prud'Homme, R.K., "Principles of nanoparticle formation by flash nanoprecipitation", Nano Today, (2016) vol. 11, No. 2, pp. 212-227.
Saberi, A.H. et al., "Fabrication of vitamin E-enriched nanoemulsions: Factors affecting particle size using spontaneous emulsification", J. Colloid & Interface Science, (2013), vol. 391, pp. 95-102.
Sacks, J.J. et al., "2010 National and State Costs of Excessive Alcohol Consumption", American J. of Preventive Medicine, (2015), vol. 49, No. 5, pp. e73-e79.
Savjani, K.T. et al., "Drug solubility: importance and enhancement techniques", ISRN Pharmaceutics, (2012), vol. 2012, Article ID 195727, pp. 1-10.
Sheela, D.L. et al., "Laurie acid induce cell death in colon cancer cells mediated by the epidermal growth factor receptor downregulation: An in silica and in vitro study", Human & Experimental Toxicology, (Epub. Apr. 3, 2019) DOI:10.1177 /0960327119839185, pp. 1-9.
Solanki, S.S. et al., "Microemulsion Drug Delivery System: For Bioavailability Enhancement of Ampelopsin", International Scholarly Research Network, ISRN Pharmaceutics, (2012) vol. 2012, Article ID 108164, pp. 1-4.
Solans, C. et al., "Nano-emulsions", Current Opinion in Colloid & Interface Science, (2005) vol. 10, Nos. 3-4, pp. 102-110.

(56) References Cited

OTHER PUBLICATIONS

Taisne, L. & Cabane, B., "Emulsification and Ripening following a Temperature Quench", Langmuir, (1998) vol. 14, No. 17, pp. 4744-4752.
Tang, C. et al., "Polymer Directed Self-Assembly of pH-Responsive Antioxidant Nanoparticles", Langmuir, (2015), vol. 31, No. 12, pp. 3612-3620.
Thanou, M. et al., Oral drug absorption enhancement by chitosan and its derivatives, Advanced Drug Delivery Reviews, (2001) vol. 52, No. 2, pp. 117-126.
Tong, Q. et al., "Determination of dihydromyricetin in rat plasma by LC-MS/MS and its application to a pharmacokinetic study", J. Pharmaceutical & Biomedical Analysis, (2015) vol. 114, pp. 455-461.
U.S. Appl. No. 16/683,387 Requirement for Restriction/Election dated Dec. 3, 2020.
U.S. Appl. No. 16/683,387 Office Action dated Jul. 14, 2021.
U.S. Appl. No. 16/683,387 Office Action dated Apr. 13, 2022.
U.S. Appl. No. 16/810,710 Requirement for Restriction/Election dated Jan. 6, 2021.
U.S. Appl. No. 16/810,710 Office Action dated May 12, 2021.
U.S. Appl. No. 16/810,710 Office Action dated Mar. 30, 2022.
U.S. Appl. No. 16/723,127 Requirement for Restriction/Election dated Jun. 1, 2021.
U.S. Appl. No. 16/723,127 Office Action dated Sep. 15, 2021.
U.S. Appl. No. 17/320,945 Office Action dated Apr. 26, 2023.
U.S. Appl. No. 17/320,945 Office Action dated Sep. 19, 2023.
U.S. Appl. No. 17/694,571 Requirement for Restriction/Election dated Jul. 20, 2023.
U.S. Appl. No. 17/694,571 Office Action dated Dec. 20, 2023.
U.S. Appl. No. 17/899,157 Requirement for Restriction/Election dated Oct. 30, 2023.
Wang, C. et al., "Enhancing bioavailability of dihydromyricetin through inhibiting precipitation of soluble cocrystals by a crystallization inhibitor", Crystal Growth & Design, (2016) vol. 16, No. 9, pp. 5030-5039.
Weissmueller, N.T. et al., "Nanocarriers from GRAS zein proteins to encapsulate hydrophobic actives", Biomacromolecules, (2016), vol. 17, No. 11, pp. 3828-3837.
Whitehead, K. & Mitragotri, S., "Mechanistic Analysis of Chemical Permeation Enhancers for Oral Drug Delivery", Pharmaceutical Research, (2008), vol. 25, No. 6, pp. 1412-1419.
Whitehead, K. et al., "Safe and Effective Permeation Enhancers for Oral Drug Delivery", Pharmaceutical Research, (2008) vol. 25, No. 8, pp. 1782-1788.
Yao, M.-J. & Huang, J.-H., "Study on the Microencapsulation of Dihydromyricetin", J. Jishou University (Natural Science Edition), (2007) vol. 28, No. 3, pp. 107-111 (English-language abstract).
Zhang, J. et al., "Recent Update on the Pharmacological Effects and Mechanisms of Dihydromyricetin", Frontiers in Pharmacol., (Oct. 25, 2018) vol. 9, article 1204, pp. 1-11, https://doi.org/10.3389/fphar.2018.01204.
Zhang, X. et al., "Evaluation and manipulation of the key emulsification factors toward highly stable PCM-water nano-emulsions for thermal energy storage", Solar Energy Materials & Solar Cells, (2021) vol. 219, No. 110820, pp. 1-11.
Zhang, X.-Y. et al., "Scavenging Effect of Dihydromyricetin on the Free Radicals by ESR", Modern Food Science & Technology, (2010) vol. 26, issue 10, pp. 1040-1042, 1070 (English-language abstract).
Zhang, Y. et al., "Design and Solidification of Fast-Releasing Clofazimine Nanoparticles for Treatment of Cryptosporidiosis", Molecular Pharmaceutics, (2017) vol. 14, No. 10, pp. 3480-3488.
Ji, Y. et al., "Effects of Fruits of Hovenia dulcis Thunb on Acute Alcohol Toxicity in Mice", J. Chinese Medicinal Materials, (2001) vol. 24, issue 2, pp. 126-128 (English-language abstract).
Ji, Y. et al., "Effects of Hovenia dulcis Thunb on Blood Sugar and Hepatic Glycogen in Diabetic Mice", J. Chinese Medicinal Materials, (2002) vol. 25, issue 3, pp. 190-191 (English-language abstract).
Fernandez, P. et al., "Nano-emulsion formation by emulsion phase inversion", Colloids & Surfaces A: Physicochem. Eng. Aspects, (2004) vol. 251, Nos. 1-3, pp. 53-58.
U.S. Appl. No. 17/618,884 Applicant Initiated Interview Summary dated Dec. 2, 2024.
U.S. Appl. No. 17/618,884 Office Action dated Jul. 8, 2024.
Lundberg, "A Supplement That May Block the Toxic Effects of Alcohol", Medscape, https://www.medscape.com/viewarticle/885865?form=fpf (Sep. 26, 2017).
Ren et al., "Dihydromyricetin protects neurons in an MPTP-induced model of Parkinson's disease by suppressing glycogen synthase kinase-3 beta activity", Acta Pharmacologica Sinica, vol. 37, pp. 1316-1324 (2016).
U.S. Appl. No. 17/618,884 Office Action dated Jun. 20, 2023.
Maher et al., "Safety and efficacy of sodium caprate in promoting oral drug absorption: from in vitro to the clinic", Advanced Drug Delivery Reviews, vol. 61, pp. 1427-1449 (2009).
PubChem, "Dihydromyricetin", 31 pages, https://pubchem.ncbi.nlm.nih.gov/compound/161557, accessed Jun. 1, 2023.
Cech et al., "Evaluating the suitability of a pH-dependent pore former in a sustained release film-coating formulation", 1st Industry meets Academla—Unlocking the Potential for Innovation, presented Apr. 13-14, 2016, https://www.pharmaexcipients.com/wp-content/uploads/2020/07/7.-Kollicoat-SR-30-D-483-Combination-with-MAE.pdf; accessed Jun. 1, 2023.
Cuomo et al., "Carbonated beverages and gastrointestinal system: Between myth and reality", Nutrition, Metabolism & Cardiovascular Diseases, vol. 19, pp. 683-689 (2009).
Shen et al., "Dihydromyricetin as a Novel Anti-Alcohol Intoxication Medication", J. Neuroscience, vol. 32, No. 1, pp. 390-401 (2012).
Baek et al., "Antioxidant Properties of a Dihydromyricetin-Rich Extract from Vine Tea (*Ampelopsis grossedentata*) in Menhaden Oil", Research & Reviews: J. Botanical Sciences, vol. 4, Iss. 3, pp. 53-63 (2015).
Liu et al., "Characterization and antioxidant activity of dihydromyricetin-lecithin complex", Eur. Food Res. Technol., vol. 230, pp. 325-331 (2009).
Liu et al., "Characterization, Stability and Antioxidant Activity of the Inclusion Complex of Dihydromyricetin With Hydroxypropyl-beta-Cyclodextrin", J. Food Biochemistry, vol. 36, pp. 634-641 (2011).
Liang et al., "Dihydromyricetin Ameliorates Behavioral Deficits and Reverses Neuropathology of Transgenic Mouse Models of Alzheimer's Disease", Neurochem. Res., vol. 39, pp. 1171-1181 (2014).
Wang et al., "Protective Effect of Dihydromyricetin Against Lipopolysaccharide-Induced Acute Kidney Injury in a Rat Model", Med. Sci. Monit., vol. 22, pp. 454-459 (2016).
Morales et al., "Hovenia dulcis Thunb. pseudofruits as functional foods: Phytochemicals and bioactive properties in different maturity stages", J. Functional Foods, vol. 29, pp. 37-45 (2017).
Antonov et al., "Entering and Exiting the Protein—Polyelectrolyte Coacervate Phase via Nonmonotonic Salt Dependence of Critical Conditions", Biomacromolecules, vol. 11, No. 1, pp. 51-59 (2010).
Bilati et al., "Development of a nanoprecipitation method intended for the entrapment of hydrophilic drugs into nanoparticles", European J. Pharmaceutical Sciences, vol. 24, pp. 67-75 (2005).
Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).
Choi et al., "Hydrophobic ion pair formation between leuprolide and sodium oleate for sustained release from biodegradable polymeric microspheres", International Journal of Pharmaceutics, vol. 203, pp. 193-202 (2000).
Crater et al., "Barrier Properties of Gastrointestinal Mucus to Nanoparticle Transport," Macromolecular Bioscience, vol. 10, No. 12, pp. 1473-1483 (2010).
Cu et al., "Drug delivery: Stealth particles give mucus the slip", Nature Materials, vol. 8, No. 1, pp. 11-13 (Jan. 2009).
Davies et al., "Recent advances in the management of cystic fibrosis", Archives of Disease in Childhood, vol. 99, No. 11, pp. 1033-1036 (2014).

(56) References Cited

OTHER PUBLICATIONS

De Azevedo et al., "Mastoparan induces apoptosis in B16F10-Nex2 melanoma cells via the intrinsic mitochondrial pathway and displays antitumor activity in vivo", Peptides, vol. 68, pp. 113-119 (2015).

Deng et al., "Janus Nanoparticles of Block Copolymers by Emulsion Solvent Evaporation Induced Assembly", Macromolecules, vol. 49, pp. 1362-1368 (2016).

Ensign et al., "Oral drug delivery with polymeric nanoparticles: The gastrointestinal mucus barriers," Advanced Drug Delivery Reviews, vol. 64, No. 6, pp. 557-570 (2012).

Extended European Search Report (EESR) dated Jan. 8, 2018 in European Application No. 15811879.4.

Galindo-Rodriguez et al., "Polymeric Nanoparticles for Oral Delivery of Drugs and Vaccines: A Critical Evaluation of In Vivo Studies", Critical Reviews in Therapeutic Drug Carrier Systems, vol. 22, No. 5, pp. 419-463 (2005).

Gessner et al., "Nanoparticles Modified with Cell-Penetrating Peptides: Conjugation Mechanisms, Physicochemical Properties, and Application in Cancer Diagnosis and Therapy", International Journal of Molecular Sciences, vol. 21, 2536, pp. 1-21 (2020).

Hoiby, "Recent advances in the treatment of Pseudomonas aeruginosa infections in cystic fibrosis", BMC Medicine, vol. 9, No. 32, pp. 1-7 (2011).

Holland et al., "Polymers for Biodegradable Medical Devices, 1. The Potential of Polyesters as Controlled by Macromolecular Release Systems", Journal of Controlled Release, vol. 4, pp. 155-180 (1986).

Johnson et al., "Chemical Processing and Micromixing in Confined Impinging Jets", AIChE Journal, vol. 49, No. 9, pp. 2264-2282 (2003).

Johnson et al., "Engineering the Direct Precipitation of Stabilized Organic and Block Copolymer Nonparticles as Unique Composites", Abstracts of Papers of the American Chemical Society, No. 441 (Abstract) (Sep. 2003).

Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).

Johnson et al., "Nanoprecipitation of Organic Actives Using Mixing and Block Copolymer Stabilization", Abstracts of Papers of the American Chemical Society, No. 186 (Abstract) (Sep. 2003).

Kader A. et al., "In Vitro Release of Theophylline from Poly(Lactic Acid) Sustained-Release Pellets. Prepared by Direct Compression.", Drug Development and Industrial Pharmacy, 24(6), 527-534 (1998).

Khanvilkar et al., "Drug transfer through mucus," Advanced Drug Delivery Reviews, vol. 48, Nos. 2-3, pp. 173-193 (2001).

Lai et al., "Mucus-penetrating nanoparticles for drug and gene delivery to mucosal tissues," Advanced Drug Delivery Reviews, vol. 61, No. 2, pp. 158-171 (2009).

Lai et al., "Rapid transport of large polymeric nanoparticles in fresh undiluted human mucus," Proceedings National Academy of Sciences, vol. 104, No. 5, pp. 1482-1487 (Jan. 30, 2007).

Lan et al. Preparation and Characterization of Super Cross-Linked Poly(ethylene oxide) Gel Polymer Electrolyte for Lithium-Ion Battery. Science of Advanced Materials, vol. 9, No. 6, pp. 988-994(7) (Jun. 2017).

Liu et al., CFD Predictions for Chemical Processing in a Confined Impinging-Jets Reactor, AIChE Journal, vol. 52, No. 2, pp. 731-744 (Feb. 2006).

Livraghi et al., "Cystic Fibrosis and Other Respiratory Diseases of Impaired Mucus Clearance", Toxicologic Pathology, vol. 35, No. 1, pp. 116-129 (2007).

Mai et al., "Controlled Incorporation of Particles into the Central Portion of Vesicle Walls", J. Am. Chem. Soc., vol. 132, pp. 10078-10084 (2010).

Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).

Muheem et al., "A review on the strategies for oral delivery of proteins and peptides and their clinical perspectives", Saudi Pharmaceutical Journal, vol. 24, No. 4, pp. 413-428 (2016).

Okuyama et al., "Preparation of functional nanostructured particles by spray drying", Advanced Powder Technol., vol. 17, No. 6, pp. 587-611 (2006).

Overbeek et al., "Phase separation in polyelectrolyte solutions. Theory of complex coacervation", Journal of Cellular Physiology, vol. 49, No. S1, pp. 7-26 (1957).

Pagels et al., "Inverse Flash NanoPrecipitation for Biologics Encapsulation: Nanoparticle Formation and Ionic Stabilization in Organic Solvents", ACS Publications, vol. 1271, pp. 249-27 4 (2017).

Pagels et al., "Polymeric nanoparticles and microparticles for the delivery of peptides, biologics, and soluble therapeutics", Journal of Controlled Release, vol. 219, pp. 519-535 & Supplemental Information (2015).

Pinkerton et al., "Formation of Stable Nanocarriers by in Situ Ion Pairing during Block-Copolymer-Directed Rapid Precipitation", Molecular Pharmaceutics, vol. 10, No. 1, pp. 319-328 (2013).

Pustulka et al., "Flash Nanoprecipitation: Particle Structure and Stability", Molecular Pharmaceutics, vol. 10, pp. 4367-4377 (2013).

Riess et al. "Emulsifying Properties of Block Copolymers. Oil-Water Emulsions and Microemulsions", Polym. Eng. Sci., vol. 17, No. 8, pp. 634-638 (1977).

Sahoo et al., "Characterization of Porous PLGA/PLA Microparticles as a Scaffold for Three Dimensional Growth of Breast Cancer Cells", Biomacromolecules, vol. 6, pp. 1132-1139 (2005).

Savjani, K.T. et al., "Drug Solubility: Importance and Enhancement Techniques", ISRN Pharmaceutics, vol. 2012, Article ID 195727, pp. 1-10 (2012).

Schwendeman et al., "Injectable controlled release depots for large molecules", Journal of Controlled Release, vol. 190, pp. 240-253 (37 pages) (Sep. 28, 2014).

Serajuddin, "Salt formation to improve drug solubility", Advanced Drug Delivery Reviews, vol. 59, No. 7, pp. 603-616 (2007).

Shah et al., Poly(glycolic acid-co-DL-lactic acid): diffusion or degradation controlled drug delivery?, Journal of Controlled Release, vol. 18, pp. 261-270 (1992).

Song et al., "A novel in situ hydrophobic ion pairing (HIP) formulation strategy for clinical product selection of a nanoparticle drug delivery system", Journal of Controlled Release, vol. 229, pp. 106-119 (2016).

The Dow Chemical Company, "Dow excipients for consumer health and pharmaceuticals", 3 pages, 2024, https://www.dow.com/en-us/document-viewer.html?randomVar=4113691100936629343&docPath=/content/dam/dcc/documents/118/118-01909-01-consumer-health-and-pharma-brochure.pdf, accessed Feb. 11, 2025.

U.S. Appl. No. 16/761,140 Notice of Allowance and Notice of Allowability dated Nov. 14, 2024.

U.S. Appl. No. 16/761,140 Examiner Initiated Interview Summary dated Nov. 14, 2024.

U.S. Appl. No. 17/320,945 Office Action dated Mar. 1, 2024.

U.S. Appl. No. 17/899,157 Office Action dated Oct. 23, 2024.

U.S. Appl. No. 17/899,157 Office Action dated Apr. 10, 2024.

Xu et aL., "Scalable method to produce biodegradable nanoparticles that rapidly penetrate human mucus", Journal of Controlled Release, vol. 170, pp. 279-286 (2013).

Xu et al., "Influence of experimental parameters and the copolymer structure on the size control of nanospheres in double emulsion method", J. Polymer Research, vol. 18, pp. 131-137 (2011).

Ya-Chen, et al., Combined Tween 20-Stabilized Gold Nanoparticles and Reduced Graphite Oxide-Fe3O4 Nanoparticle Composites for Rapid and Efficient Removal of Mercury Species from a Complex Matrix, 2014, ACS Appl. Mater. Interfaces, 6, 17437-17445 (2014).

Zandonella, "Bob Prud'homme—Flash NanoPrecipitation" http://research.princeton.edu/news/features/a/index.xrnl?id=6234, accessed Mar. 9, 2018, originally published Dec. 9, 2011, pp. 1-2.

Zhou et al., "PEG-b-PCL polymeric nano-micelle inhibits vascular angiogenesis by activating p53-dependent apoptosis in zebrafish", International Journal of Nanomedicine, vol. 11, pp. 6517-6531 (2016).

(56) References Cited

OTHER PUBLICATIONS

Zhu et al., "Preparation and characterization of hCG-loaded polylactide or poly(lac:tide-co-glycolide) microspheres using a modified water-in-oil-in-water (w/o/w) emulsion solvent evaporation technique", J. Microencapsulation, vol. 18, No. 2, pp. 247-260 (2001).

\* cited by examiner

DIHYDROMYRICETIN HOT MELT EXTRUSION FORMULATIONS AND METHODS FOR FORMING THEM

This application is a continuation of U.S. application Ser. No. 16/683,387, filed Nov. 14, 2019, which claims the benefit of U.S. Provisional Application No. 62/767,208, filed Nov. 14, 2018, which are hereby incorporated by reference in their entireties.

FIELD OF THE INVENTION

The invention pertains to compositions including dihydromyricetin (DHM) and methods for forming them, including hot melt extrusion.

BACKGROUND

Alcohol is a constituent of medicines, foods, and beverages that provides both beneficial and detrimental effects on human beings. Alcohol can refer to ethyl alcohol (ethanol), which is the common form of consumable alcohol found in alcoholic beverages, e.g., such as beer, wine, and liquor. During consumption, alcohol is rapidly absorbed from the stomach and small intestine into the bloodstream, from which it can affect several organs, including the brain, heart, pancreas, and liver. Alcohol can act as a depressant to the central nervous system (CNS). For example, alcohol interferes with the brain's communication pathways, which affects brain functionality that manifests in cognitive and behavioral changes, e.g., such as a person's ability to think, focus, and move, as well as his/her mood and behavior. Alcohol can cause inflammation and damage to the liver, e.g., consistent heavy drinking can cause chronic liver problems. For example, heavy drinking can lead to steatosis (e.g., fatty liver), infection (e.g., alcoholic hepatitis), fibrosis, and cirrhosis. More commonly, even a single instance of light to moderate to heavy alcohol consumption can result in what is commonly known as an 'alcohol hangover'. A hangover refers to an array of physical symptoms that affect a person shortly after ingesting alcohol, e.g., within hours of consumption. The symptoms of a hangover include, for example, one or more of thirst, fatigue and/or weakness, headache and/or muscle aches, dizziness/faintness, loss of appetite, poor and/or decreased sleep, nausea and/or stomach pain (e.g., which can include vomiting), and elevated heart rate. A hangover is considered to be one of the most widely experienced negative consequences of consuming ethanol.[1]

SUMMARY OF INVENTION

In an embodiment of the invention, a dihydromyricetin (DHM) formulation includes dihydromyricetin (DHM) and a matrix material. The matrix material can include a polymer. For example, the polymer can be hydroxypropyl methyl cellulose (HPMC), cellulose ester, cellulose acrylate, methyl cellulose, ethyl cellulose, hydroxyethyl cellulose, hydroxypropylcellulose (HPC), hydroxypropyl methylcellulose propionate succinate, hydroxypropyl methyl cellulose phthalate (HPMCP), hydroxypropyl methyl cellulose acetate succinate (HPMCAS), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), carboxymethylcellulose, carboxymethylcellulose salt, sodium carboxymethylcellulose, a cellulose polymer, and/or combinations.

The polymer can also be polyethylene oxide (PEO), a polyoxyethylene-polyoxypropylene block copolymer (a poloxamer), a polyoxyethylene alkyl ether, a polyoxyethylene castor oil, a low molecular-weight oligomer of polyethylene glycol, an ethylene glycol-vinyl glycol copolymer, a polyoxyethylene castor oil, an ethoxylated castor oil, a polyoxyl hydrogenated castor oil, a polyoxyl 40 hydrogenated castor oil, a polyethoxylated sorbitan, polyoxyethylene sorbitan monooleate, and/or combinations.

In an embodiment of the invention, the matrix material includes polyvinyl pyrrolidone (PVP). In an embodiment of the invention, the matrix material includes poly(vinyl pyrrolidone-co-vinyl acetate) (PVP-VA).

The matrix material can include a polymer. The polymer can be poly(methyl methacrylate) (PMMA), low molecular weight poly(methyl methacrylate), polymethacrylate, methacrylic acid copolymers, a polymethacrylate derivative, poly(methacrylic acid-co-methyl methacrylate) 1:1, poly(methacrylic acid-co-methyl methacrylate) 1:2, poly(methacrylic acid-co-ethyl acrylate) 1:1, and/or combinations. The polymer can also be polycaprolactam, polycaprolactone (PCL), polylactic acid (PLA), polyglycolic acid (PGA), poly(lactic-glycolic acid) (PLGA), and/or combinations.

The matrix material can include a material, such as a wax, low melting point waxes such as carnauba wax, starch, starch derivatives, sugars, sugar alcohols, leucine, lipids, a polyol, a polyether, fructose, glucose, lactose, mannitol, trehalose, sucrose, raffinose, maltitol, lactitol, sorbitol, xylitol, erythritol, xylose, acorbose, melezitose, galactose, melibrose, isomaltose, a natural sugar extracts, malt beet sugar, corn sugar, high-fructose corn syrup, a sugar oligomers, polydextrose and dextrans with molecular weights less than 10,000 Daltons, a polyol, glycerol, sorbitol, ethylene glycol, propylene glycol, butanediol, polymeric derivatives of vitamin E, poly(propylene), and combinations.

The DHM formulation can further include a plasticizer. The plasticizer can include a plasticizer, for example, triacetin, citrate ester, triethyl citrate, acetyl triethyl citrate, tributyl citrate, and combinations. The plasticizer can also be low molecular weight polyols having aliphatic hydroxyls, poly(propylene glycol), low molecular weight poly(ethylene oxide) having an average molecular weight of less than about 500,000 Da, poly(ethylene glycol), D-alpha tocopheryl PEG 1000 succinate (TPGS), low molecular-weight polyethylene glycol, propylene glycol, 1,2-butylene glycol, 2,3-butylene glycol, triethylene glycol, tetraethylene glycol, mono propylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, allyl glycolate, vitamin E, and/or pressurized $CO_2$.

The DHM formulation can further include a permeabilizer. The permeabilizer can include caprylic acid, a caprylate salt, and/or sodium caprylate. The permeabilizer can also include a permeabilizer such as a fatty acid, a saturated fatty acid, and/or a fatty acid complexed with a cation, such as a metal cation, a metal divalent cation, a magnesium divalent cation, a calcium divalent cation, a zinc divalent cation, an iron divalent cation, a metal trivalent cation, an iron trivalent cation, a fatty acid salt, a fatty acid metallic soap, and combinations.

The DHM formulation can further include an antioxidant. The DHM formulation can further include a coactive such as glutathione, L-cysteine, N-acetyl cysteine (NAC), Prickly Pear extract, Milk Thistle, ginger root, vitamin B, vitamin C, vitamin E, an electrolyte, a sugar, and combinations.

The DHM formulation can further include a pH buffering agent. The pH buffering agent can be an acidic pH buffering agent, citric acid, a citrate salt, a sodium citrate, a potassium citrate, calcium citrate, and/or combinations.

In an embodiment of the invention, in the DHM formulation, the DHM is not solubilized or dissolved by an aqueous solution having a pH of at most 3.5, and the DHM is solubilized or dissolved by an aqueous solution having a pH of at least 5.5. In an embodiment of the invention, the DHM comprises at least 20 wt % of the powder. In an embodiment of the invention, the crystallinity of the DHM is at most 10%. In an embodiment of the invention, the DHM formulation is homogeneous.

In an embodiment of the invention, a dosage form includes the DHM formulation and an enteric coating that encapsulates the DHM formulation. The enteric coating can be a polymeric coating or a methacrylate copolymer coating.

In an embodiment of the invention, a dosage form includes the DHM formulation of in a powder form and an aqueous liquid or a gel. The DHM formulation can be in a powder form which is mixed with or suspended in the aqueous liquid or the gel.

In an embodiment of the invention, in the DHM formulation, the matrix material is poly(vinyl pyrrolidone-co-vinyl acetate) (PVP-VA) and the DHM comprises at least 20 wt % of the DHM formulation.

In an embodiment of the invention, a method for forming the dihydromyricetin (DHM) includes: mixing the dihydromyricetin (DHM) and the matrix material to form a compounding mixture; processing the compounding mixture in an extruder to form an extrudate; and collecting the extrudate as the dihydromyricetin (DHM) formulation. The operating temperature of the extruder can be less than the melting temperature of dihydromyricetin (DHM).

In an embodiment of the invention, a method for reducing hangover symptoms includes: administering the dihydromyricetin (DHM) formulation to a patient suffering from hangover symptoms, so that the patient's hangover symptoms are reduced.

In an embodiment of the invention, the dihydromyricetin (DHM) formulation can be used in preventing an alcohol use disorder, preventing alcoholism, treating an alcohol use disorder, treating alcoholism, or treating an alcohol overdose.

In an embodiment of the invention, the dihydromyricetin (DHM) formulation can be used in increasing antioxidant capacity, neuroprotection, preventing Alzheimer's disease, treating Alzheimer's disease, inhibiting inflammation, protecting the kidney, protecting the liver, preventing or treating cancer, ameliorating a metabolic disorder, preventing diabetes, treating diabetes, or treating a bacterial infection.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated.

An embodiment of the present invention includes a method to improve the bioavailability of the molecule dihydromyricetin (DHM) through the process known as hot melt extrusion (HME) to form a hot melt extruded formulation. This method can include processing by HME of a combination of materials including DHM, additional beneficial molecules (e.g., co-actives), polymeric excipients, plasticizers, and permeability-enhancing compounds (permeabilizers). The final form of the product may comprise powders, granules, or tablets to be used in further formulations.

The present invention can provide a hot-melt extrusion method and resultant formulation including a beneficial amount of DHM, additional beneficial molecules, polymeric excipients, plasticizers, and permeability-enhancing compounds. Improvements in bioavailability and pharmacokinetic parameters of DHM can be associated with this formulation method.

In an embodiment, the formulation may be processed further in forms beyond powders, granules, and tablets for administration by various routes either by self-administration or administration by any number of routes known to a skilled artisan. In some embodiments, the formulation may be well suited to oral administration routes.

Thomson, et al. (U.S. Pat. No. 3,239,370) discusses a method and process for coating substrates with films of molten random copolymer of ethylene and carboxylic acid. The polymer is hot melt extruded through a slit die to provide the film that is applied to a substrate in molten form before cooling into a solid state. [9] Schippers, et al. (U.S. Pat. No. 3,410,938) discusses processing thermoplastic polymers by conveying them down the barrel of a hot metal extruder by screw extrusion to remove trapped gases within the polymer and generate various morphologies of the polymer being processed.[10] McGinity, et al. (U.S. Pat. No. 6,488,963B1) discusses hot melt extrudable pharmaceutical formulations, which include therapeutic molecules dispersed within a high molecular weight poly(ethylene oxide) (PEO) matrix and may include plasticizers. [11] Miller, et al. (U.S. Pat. No. 9,504,658, U.S. Ser. No. 11/718,620) discusses dispersions of fine drug particles within polymeric and/or lipophilic polymeric matrices, e.g., of PEO, which can include other hydrophilic polymers, e.g., hydroxypropyl methylcellulose (HPMC) and polyvinyl acetate (PVA), that are processed by HME. [12] Alderman, et al. (U.S. Pat. No. 4,678,516) discusses a method for prolonging the release of therapeutically active molecules by dispersing them within a thermoplastic polymeric matrix consisting of hydroxypropyl methylcellulose (HPMC) and plasticizers. [13] Brough, et al. (U.S. Pat. No. 8,486,423, U.S. Ser. No. 12/196,154) discusses a method of dispersing pharmaceutically relevant active ingredients (APIs) into homogeneous composites, including thermoplastic polymers that can molecularly dissolve the API or provide a matrix for dispersion of fine particles of the API, that can be further processed by hot melt extrusion. [14] Fischer, et al. (U.S. Pat. No. 8,298,581, U.S. Ser. No. 10/550,685) discusses a matrix composition for the delivery of APIs as oral formulations and a double-coating process including a polymer from the PEO group and a polymer from a copolymer of ethylene oxide and propylene oxide.[15] Yang, et al. (U.S. Pat. No. 8,603,514, U.S. Ser.

No. 11/775,484) and Fuisz, et al. (US Pat. Applic. Pub. 2007-0281003 A1, U.S. Ser. No. 11/674,223) discuss pharmaceutically relevant compositions for the formation of films containing one or more entrapped APIs and other excipients or plasticizers in a polymeric matrix by HME.[16, 17] Bernstein, et al. (U.S. Pat. No. 6,730,322B1) discusses the integration of hydrophobic components into a microsphere polymeric matrix to alter the release characteristics of entrapped drugs. McAllister, et al. (US Pat. Applic. Pub. 2003-0049311 A1, Ser. No. 10/060,603) and McAllister, et al. (U.S. Pat. No. 7,842,308, Ser. No. 10/470,439) discuss pharmaceutical formulations for injection molding and polymeric matrices for film formation.[18-20]

Dihydromyricetin (DHM)

Dihydromyricetin (DHM), a flavonoid compound isolated from the Hovenia plant can "sober-up" rats inebriated with alcohol[2], prevent predisposed rats from becoming alcoholics[2], return alcoholic rats to baseline levels of alcohol consumption[2], reduce hangover symptoms[2], and prevent fetal alcohol spectrum disorders in the offspring of rats exposed to significant amounts alcohol during pregnancy.[2] DHM can be dissolved in a solvent, such as dimethylsulfoxide (DMSO). DHM can be complexed with a metal, such as a divalent alkali earth metal, divalent magnesium (Mg(II), $Mg^{+2}$), a divalent transition metal, divalent iron (Fe(II), $Fe^{+2}$), divalent copper (Cu(II), $Cu^{+2}$), a trivalent transition metal, or trivalent iron (Fe(III), $Fe^{+3}$) DHM has unique physicochemical properties including low solubility, high hydroxyl functional group content, and unknown thermal stability, rendering the processing of DHM and other flavonoids under hot melt extrusion (HME) conditions difficult.

DHM demonstrates pharmacological properties for successful medical treatment of alcohol use disorders (AUDs) [21-23]. Given limited available pharmacotherapies for AUDs and these being limited by low patient compliance, because of the adverse effects they may cause, therapies for the treatment of AUDs should be advanced, e.g., through DHM therapeutic strategies.[24]

In addition to DHMs potential for the treatment of AUDs, which, without being bound by theory, may be achieved through DHM's inhibiting the effect of alcohol on $GABA_A$ receptors ($GABA_A$Rs) in the brain, DHM and the Hovenia plant it is isolated from have shown efficacy in mitigating liver injuries[25-27], decreasing alcohol and acetaldehyde concentrations in the blood via enhancing ADH and ALDH activity[28, 29], and eliminating alcohol-induced excessive free radicals.[30] DHM has been observed to have oxidative stress-mediating activity, i.e., increase antioxidant capacity for scavenging reactive oxygen species, which may result in neuroprotective, nephroprotective (kidney protecting), and hepatoprotective (liver protecting) effects, which may ameliorate, for example, the effects of hypobaric hypoxia, side effects of the chemotherapeutic agent cisplatin, and detrimental effects of ethanol. DHM may have a neuroprotective role in Alzheimer's and Parkinson's diseases. DHM can also inhibit inflammation. DHM can also have anticancer activity and regulate cell proliferation and apoptosis. DHM can mediate metabolism, and may be useful in ameliorating certain metabolic disorders, such as diabetes, weight gain, hyperlipidemia, and atherosclerosis. DHM exhibits antibacterial activity (Li, H. et al., "The Versatile Effects of Dihydromyricetin in Health", Evidence Based Complementary & Alternative Medicine 2017, Art. ID 1 053617).

A DHM formulation designed to reduce alcohol's negative effects when taken after alcohol consumption is covered under U.S. Pat. No. 9,603,830 B2 (granted on Mar. 28, 2017) and is sold in the US under the brand name Thrive+®.

Despite promising results in rats, one challenge in translating DHM's efficacy to humans in a commercially viable way is DHM's oral bioavailability of less than 5% [31]. DHM can have poor stability. DHM is a BCS class IV drug limited by having the properties of low solubility and low permeability. In the context of successfully commercialized drugs, DHM requires large doses for efficacy. Because DHM is a naturally occurring organic compound isolated from an herb, a DHM formulation can be classified as a food (or dietary supplement) under the Dietary Products designation.

This invention addresses the problem of poor bioavailability and stability of DHM through the use of hot melt extrusion (HME). By dispersing DHM within a set of excipients using HME, e.g., excipients which are preferably chiefly polymeric, DHM can have higher supersaturation, and may exhibit increased bioavailability, be released more slowly upon ingestion, and exhibit enhanced dissolution and release kinetics, longer sustained release, higher concentrations, and improved stability with respect to low pH gastric juices and enzymes, which can cause degradation and quenching of DHM activity, than when administered in a pure form. Furthermore, the DHM HME formulation may possess improved ability to penetrate intestinal barriers, to allow DHM to reach the bloodstream more effectively and efficiently.

Hot Melt Extrusion

Hot melt extrusion ('HME') is an industrial process that can be used to create uniform polymer products such as tubes, sheets, and foams.[3-7] HME can be employed to disperse active pharmaceutical ingredients (APIs) within solid polymer matrices.[3, 5, 6] In this process, an API and polymer excipient(s) are fed into an extruder. These are then conveyed by single or double-screws down the barrel of the device while undergoing melting, mixing, dispersing, and finally cooling processes.

HME can be used to confer improved bioavailability and API dissolution in a final application. A limitation of HME is that the active compound and excipient(s) are subjected to elevated temperatures which may prompt or accelerate degradation of an API.

The term "hot-melt extrudable" refers to a compound or formulation that may be hot-melt extruded. A hot-melt extrudable polymer is one that is sufficiently rigid for an intended use at standard ambient temperature and pressure, but is capable of deformation or forming a liquid or semi-liquid state under elevated heat or pressure.

In an embodiment of the invention, a composition for hot-melt extrusion does not include a plasticizer. In another embodiment of the invention, a composition for hot-melt extrusion includes one or more plasticizers. Although the process according to the invention has been called a hot-melt extrusion, other equivalent and similar processes such as injection molding, hot dipping, melt casting, and compression molding may be used. By using any of these methods, the formulation may be shaped as needed according to the desired mode of administration, e.g. powders, tablets, pills, lozenges, suppositories, capsules and the like. The hot-melt extrusion process employed in some embodiments of the invention is conducted at an elevated temperature, i.e., the heating zone(s) of the extruder is above room temperature (about 20° C.). An operating temperature range should be selected that minimizes the degradation or decomposition of the therapeutic compound (e.g., DHM) during processing. For example, the operating temperature range can be in the range of from about 60° C. to about 160° C. and can be set for one or more extruder heating zone(s).

In a hot-melt extrusion (HME) process according to the invention an effective amount of therapeutic compound(s) is mixed with matrix polymer(s), a plasticizer, such as polyethylene glycol (PEG), permeability-enhancers, and/or other excipients. Other components may be added for various embodiments of the invention. The mixture is then placed in the extruder hopper and passed through the heated area of the extruder at a temperature which melts or softens the matrix polymer, excipient(s), and/or plasticizer, if present, to form a matrix throughout which the therapeutic compound is dispersed. The molten or softened mixture then exits via a die, or other such element, at which time the mixture (now called the extrudate) begins to harden. Since the extrudate is still warm or hot upon exiting the die, it may be easily shaped, molded, chopped, ground, shaped into beads, cut into strands, tableted, or otherwise processed to the desired physical form. The extruder used to practice the invention may be any commercially available or custom-built model equipped to handle dry feed and having a solid conveying zone, one or multiple heating zones, and an extrusion die. A two-stage Single Screw extruder, such as that manufactured by C.W. Brabender Instruments Incorporated (NJ), is one such apparatus. It can be advantageous for the extruder to possess multiple separate temperature controllable heating zones.

Several conditions may be varied during the extrusion process to arrive at a particularly advantageous formulation. Such conditions include, by way of example, formulation composition, feed rate, operating temperature, extruder screw RPM, residence time, die configuration, heating zone length, and/or extruder torque and/or pressure.

For example, the extrusion conditions may be selected to produce a formulation that is a homogeneous, e.g., DHM is homogeneously dispersed in a matrix material or in a combination of matrix material(s), plasticizer(s), and/or permeabilizer(s).

HME can produce various forms of solid dispersions. These may include, but are not limited to, pharmaceutically-relevant dosage forms, such as powders, pellets, cylinders, tubes, granules, and flakes. These can be processed further into a desired morphology with desired surface characteristics.

In an embodiment of the present invention, the use of hot melt extrusion in the preparation of pharmaceutical dosage forms to effectively deliver DHM has several advantages. HME is scalable, e.g., it can be used at the lab scale, the pilot plant scale, and to mass produce large quantities of product. It allows for DHM to be formulated with a wide variety of excipient(s) and plasticizer(s) to allow for maximum effectiveness as needed for various administration routes. Furthermore, HME can be solvent free, thus reducing the need for a subsequent solvent removal step and reducing the potential for solvent-induced toxicity.[7]

The invention includes, but is not limited to, a combination of materials including the active ingredient DHM and/or other flavonoids, additional active molecules and co-actives, permeability enhancers, excipients (including matrix materials), plasticizers, and an enteric coating. In an embodiment, the HME dosage form includes dihydromyricetin (DHM) and a coactive, such as L-cysteine, N-acetyl cysteine (NAC), Prickly Pear extract, Milk Thistle, ginger root, vitamin B, vitamin C, vitamin E, an electrolyte, a sugar, an antioxidant, and/or glutathione.

Permeability-Enhancers

A permeability-enhancer or permeabilizer is an agent that enhances the permeation of a drug compound through the epithelial cell layer in the gastrointestinal (GI) tract and, hence, enhances the amount of drug entering the bloodstream. Permeability-enhancers have been reviewed by Aungst and Whitehead[32-35]. The list of agents presented by Aungst in Table I and Whitehead in Table I are incorporated into this patent in their entirety.

Examples of permeability-enhancers are fatty acids, a saturated fatty acid, caprylic acid, a caprylate salt, sodium caprylate, a fatty acid complexed with a cation, such as a metal cation, a metal divalent cation, a magnesium (Mg(II), $Mg^{+2}$), calcium (Ca(II), $Ca^{+2}$), or zinc divalent cation (Zn (II), $Zn^{+2}$), iron divalent cation (Fe(II), $Fe^{+2}$), a metal trivalent cation, iron trivalent cation (Fe(III), $Fe^{+3}$), a fatty acid salt, a fatty acid metallic soap, and combinations of these. For example, capric acid and its salts are permeabilizers that are currently clinically approved for use in an ampicillin suppository. The caprates and other long-chain saturated fatty acids and their salts can be incorporated into the hot melt extrusion (HME) process. Their hydrophobicity can be enhanced by complexing them, for example, with divalent cations such as those of magnesium (Mg(II), $Mg^{+2}$), calcium (Ca(II), $Ca^{+2}$), or zinc, divalent iron, or trivalent iron. Permeabilizers are optional additions to the formulation. When they are used, the mass ratios of permeabilizer to DHM in the hot melt extruded formulation (extrudate) produced can range from 1:100 to 100:1.

Excipients and Matrix Materials

Excipients and matrix materials are defined as materials that aid in the formulation, stability, and/or release characteristics of the active molecule DHM. For example, homopolymers, copolymers, and amphiphilic copolymers can be used as excipients and matrix materials. The matrix material can constitute from 0.1 wt % to 99 wt % of the combined mass of the active agent(s) and excipients by weight of the final solid form. When it is desirable for the matrix material to prevent aggregation of the active domains into larger aggregates, the matrix material can constitute more than 20% or more than 40% of the combined mass of the active agent(s) and matrix material.

Exemplary excipients and matrix materials include low melting point waxes such as carnauba wax, cellulose, methyl cellulose, ethyl cellulose, polyvinylpyrrolidone (PVP) and its copolymers such as polyvinylpyrrolidone-vinyl acetate (PVP-VA), poly(ethylene-co-vinyl acetate), various grades of polyethylene glycol (PEG), polyethylene oxide (PEO), cellulose esters, cellulose acrylates, cellulose derivatives, polymethacrylate, polymethacrylate derivatives, polyoxyethylene-polyoxypropylene block copolymers (also referred to as poloxamers), hydroxypropylcellulose (HPC), hydroxypropyl methylcellulose (HPMC), HPMC derivatives, polylactic acid (PLA), poly(glycolide) (PGA), and poly(lactide-co-glycolide) (PLGA), poly(caprolactone) (PCL), starch, starch derivatives, sugars, sugar alcohols, waxes, leucine, lipids, carboxymethylcellulose, sodium carboxymethylcellulose, carboxymethylcellulose salts, hydroxyethylcellulose, methacrylic acid copolymers, poly(methyl methacrylate) (PMMA), and ethylene glycol-vinyl glycol copolymer.

Examples of excipients and matrix materials include polyoxyethylene alkyl ethers, polyoxyethylene castor oils, polycaprolactam, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), poly(methacrylic acid-co-methyl methacrylate) 1:1 (e.g., Eudragit® L100, Evonik Industries AG), poly(methacrylic acid-co-methyl methacrylate) 1:2 (e.g., Eudragit® S100), poly(methacrylic acid-co-ethyl acrylate) 1:1 (e.g., Eudragit® L100-55), a polyol, a polyether, a cellulosic polymer, sugars and sugar alcohols, for example, fructose, glucose, lactose, mannitol, trehalose, sucrose, raffinose, maltitol, lactitol, sorbitol, xylitol, erythritol, xylose, acorbose, melezitose, galactose, melibrose, and isomaltose, natural sugar extracts, for example, malt beet sugar, corn sugar, high-fructose corn syrup, sugar oligomers, such as polydextrose and dextrans with molecular weights less than 10,000 Daltons, polyols such as glycerol, sorbitol, ethylene glycol, propylene glycol, butanediol, and other oligomers, low molecular-weight oligomers, such as low molecular weight polyethylene glycol and low molecular weight poly(methyl methacrylate), ethoxylated castor oil, polyoxyl hydrogenated castor oil, polyoxyl 40 hydrogenated castor oil, polymeric derivatives of vitamin E, polyethoxylated sorbitan, and polyoxyethylene sorbitan monooleate.

The excipients and matrix materials can include amphiphilic block copolymers, for example, polystyrene-block-polyethylene glycol (PS-b-PEG), polylactic acid-block-polyethylene glycol (PLA-b-PEG), and poly(lactic-co-glycolic acid)-block-polyethylene glycol (PLGA-b-PEG).

Examples of excipients and matrix materials include derivatives of the above, copolymers of the above, and combinations of the above.

In an embodiment, the matrix material includes components with a molecular weight of less than 1,000,000 Daltons (Da), less than 100,000 Daltons, less than 10,000 Daltons, less than 5000 Daltons, or less than 2000 Daltons.

The matrix material can include a polymer. A polymer is formed of several monomer units bound to each other. For example, a polymer can be a linear polymer, a branched polymer, or a cyclic polymer. In a cyclic polymer, a set of monomers can be bound to each other to form a ring. In a noncyclic polymer, there is no set of monomers that are bound to each other to form a ring (although atoms within a given monomer unit of the polymer still may be in a ring structure, e.g., a cyclopentyl, furan, furanose, cyclohexyl, pyran, pyranose, benzene, or saccharide structure). For example, cyclodextrin is a cyclic polysaccharide. By contrast, cellulose is a linear polysaccharide formed of several hundred to many thousands of D-glucose monomers. Gum arabic includes arabinogalactan, formed of arabinose and galactose monomers.

Certain polymeric excipients and matrix materials marketed under trade names by manufacturers may include the following: BASF: Povidones, copovidones, methacrylic acid copolymers, ethylene glycol-vinyl glycol copolymers, Poloxamer 407, Poloxamer 188, poly ethylene glycols, polyoxyl 40 hydrogenated castor oils, and polymeric derivatives of vitamin E marketed by BASF under trade names SOLUPLUS, KOLLIDON VA 64, KOLLIDON 12 PF, KOLLIDON 17 PF, KOLLIDON 30, KOLLIDON 90 F, KOLLIDON SR, KOLLICOAT MAE 100P, KOLLICOAT IR, KOLLICOAT PROTECT, KOLLIPHOR P 407, KOLLIPHOR P407 MICRO, KOLLIPHOR P188, KOLLIPHOR P188 MICRO, KOLLISOLV PEG, KOLLIPHOR RH 40, KOLLIPHOR TPGS.

The Dow Chemical Company: Polymers with trade names METHOCEL, ETHOCEL, POLYOX, and AFFINISOL marketed by the Dow Chemical Company. Evonik Corporation: Polymers with trade names EUDRAGIT (methacrylates) and RESOMER, marketed by Evonik Corporation.

Ashland: Polymers with trade names AquaSolve hypromellose acetate succinate, Aqualon ethylcellulose, Aqualon sodium carboxymethylcellulose, Aquarius control film coating systems, Aquarius prime film coating systems, Aquarius protect film coating systems, Aquarius film coating systems, Aquarius preferred film coating systems, Benecel methylcellulose and hypromellose, Blanose sodium carboxymethylcellulose, CAVAMAX native cyclodextrins, Cavitron cyclodextrin, CAVASOL cyclodextrin, Klucel hydroxypropylcellulose, Natrosol hydroxyethylcellulose, Pharmasolve N-methyl-2-pyrrolidone, Plasdone S-630 copovidone, Plasdone povidone, and Polyplasdone crospovidone (cross linked polyvinyl N-pyrrolidone) marketed by Ashland Global Holdings Inc.

The foregoing lists of materials are not intended to indicate that all of these materials are equivalent and/or equally suitable.

The polymer matrix material can have a glass transition temperature (Tg) of at least 50° C., 60° C., 70° C., 80° C., 90° C., 100° C., 110° C., 115° C., 120° C., 125° C., 130° C., 150° C., 175° C., 200° C., or 250° C. For example, hydroxypropyl methyl cellulose acetate succinate (HPMCAS) has a glass transition temperature (Tg) of about 120° C.

The polymer matrix material may be selected to adjust the formulation's release profile, e.g., to adjust the rate at and duration of time over which the formulation releases an active pharmaceutical ingredient (API), such as DHM.

In an embodiment, polymers, such as one or more of those listed above, may also be incorporated as enteric coatings which coat a final tablet form of a DHM hot-melt extruded (HME) formulation and provide additional stability or sustained release benefits. For example, including an enteric coating in the formulation may alter the formulation's release profile, e.g., may alter the rate at and duration of time over which the formulation releases an active pharmaceutical ingredient (API), such as DHM. For example, the enteric coating may be a methacrylate copolymer coating.

Plasticizer

The term "plasticizer" includes compounds capable of plasticizing the polymeric excipients, including the polymer matrix material, used. The plasticizer may lower the glass transition temperature or softening point of the excipient(s) in order to allow for lower processing temperature, extruder torque, and pressure during the hot-melt extrusion (HME) process. Plasticizers, such as PEG and low molecular weight PEO, can broaden the average molecular weight of the polymeric excipients used, thereby lowering the glass transition temperature or softening point of the composition being extruded. Plasticizers can reduce the viscosity of a polymer melt, thereby allowing for lower processing temperature and extruder torque during hot-melt extrusion. A plasticizer may impart advantageous physical properties to the extruded formulation. As used herein, the term "low molecular weight PEO" means poly(ethylene oxide) homopolymer having an average molecular weight less than about 500,000.

In an embodiment according to the invention, the composition that undergoes hot melt extrusion (HME) and the extruded formulation do not include a plasticizer. In an embodiment according to the invention, the composition that undergoes hot melt extrusion (HME) and the extruded formulation include a plasticizer.

Including a plasticizer in the formulation may alter the formulation's release profile, e.g., may alter the rate at and duration of time over which the formulation releases an active pharmaceutical ingredient (API), such as DHM. Increasing the amount of plasticizer in the formulation may increase the release rate of the therapeutic compound (API, e.g., DHM). A combination of plasticizers may be used in the composition to be extruded and the extruded formulation.

Plasticizers that may be used in an embodiment of the invention include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene oxide) (e.g., having an average molecular weight of less than about 500,000 Da), and poly(ethylene glycol).

Plasticizers that may be used in an embodiment of the invention include, but are not limited to triacetin, citrate ester, vitamin E, D-alpha tocopheryl PEG 1000 succinate (TPGS), molecular surfactants, low molecular-weight polyethylene glycol, pressurized $CO_2$, propylene glycol, 1,2-butylene glycol, 2,3-butylene glycol, styrene, a glycol, triethylene glycol, tetraethylene glycol and other poly(ethylene glycol) compounds, mono propylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, triethyl citrate, acetyl triethyl citrate, tributyl citrate, and allyl glycolate.

Examples of plasticizers include derivatives of the above, copolymers of the above, and combinations of the above.

The foregoing lists of materials are not intended to indicate that all of these materials are equivalent and/or equally suitable.

The amount of plasticizer used in the formulation may affect the formulation's properties. The amount of plasticizer selected for use in the composition for HME and the formulation produced can will depend upon the plasticizers composition, physical properties, effect upon the excipient(s), interaction with other components of the formulation, ability to solubilize the therapeutic compound, and/or other factors.

Composition of the Components

In some embodiments, DHM constitutes at least 0.1 wt %, 1 wt %, 2 wt %, 3 wt %, 5 wt %, 7 wt %, 10 wt %, 15 wt %, 20 wt %, 25 wt % 30 wt %, 35 wt %, 40 wt %, 50 wt %, 55 wt %, 60 wt %, 70 wt %, 80 wt %, 90 wt %, 95 wt %, 98 wt %, or 99 wt % of the HME formulation, relative to the total mass of the formulation, including all other excipients and matrix materials.

In some embodiments, the concentration of all other components, and particularly excipients and matrix materials, in the formulation may range from 0.001 wt % to 0.01 wt %, or from 0.01 wt % to 0.1 wt %, or from 0.1 wt % to 1 wt %, or from 1 wt % to 10 wt %, or from 10 wt % to 99.9 wt %, depending on the desired release profile, the pharmacological activity and toxicity of the therapeutic compound, such as DHM and any coactive, and other such considerations.

Administration

The resulting formulations of embodiments of the present invention are useful and suitable for delivery in animals and humans and may be administered by a variety of methods. Such methods include, by way of example and without limitation: oral, nasal, buccal, rectal, ophthalmic, otic, urethral, vaginal, or sublingual dosage administration. Such methods of administration and others contemplated within the scope of the present invention are known to the skilled artisan. In vivo stability of the present formulation may vary according to the physiological environment to which it is exposed and the matrix material, excipients, and plasticizer used. Therefore, the necessity for or frequency of readministration may be different for various formulations.

The formulation of the present invention may be provided in a variety of ways, for example, powder, tablet, and capsule dosage forms. Additional components that would not significantly prohibit the hot-melt extrusion (HME) process may be added to the formulation prior to hot-melt extrusion. That is, such additional components should still allow for formulation using the hot-melt extrusion process.

For oral, buccal, and sublingual administration, the formulation may be in the form of a gel cap, caplet, tablet, capsule, suspension, or powder. Alternatively, the formulation may be in the form of a mixture with or suspension in, e.g., a DHM-containing powder according to an embodiment of the invention mixed with or suspended in, a consumable (edible) liquid (e.g., an aqueous liquid, such as water), such as a drink or liquid concentrate. Alternatively, the formulation may be in the form of a mixture with or suspension in, e.g., a DHM-containing powder according to an embodiment of the invention mixed with or suspended in, an edible gel. For rectal administration, the formulation may be in the form of a suppository, ointment, enema, tablet, or cream for release of compound into the intestines, sigmoid flexure, and/or rectum.

In solid dosage forms, the compounds can be combined with conventional carriers, for example, one or more of the following: binders, such as acacia, corn starch, or gelatin; disintegrating agents, such as corn starch, guar gum, potato starch, or alginic acid; lubricants, such as stearic acid or magnesium stearate; and inert fillers, such as lactose, sucrose, or corn starch.

It is contemplated that either one or a combination of long-acting, sustained-release, controlled-release, and/or or slow-release dosage forms may be used in the present invention. This may be desirable, if continuous exposure of an animal or a human to the active ingredient(s) (e.g., DHM) is the desired outcome. The polymers and formulations useful in this case can include derivatized cellulosic polymers of the type described in the Dow Chemical Company Technical Bulletin "Using Dow Excipients for Controlled Release of Drugs in Hydrophilic Matrix Systems", 2006 and marketed under the trade name METHOCEL (methylcellulose and hydroxypropyl methylcellulose (HPMC) polymers). The course and duration of administration of and the dosage requirements for the formulation of the present invention will vary according to the animal or human being treated, the formulation used, the method of administration used, the severity of the condition being treated, the co-administration of other drugs, and other factors.

Increased bioavailability can be achieved using HME processing by tuning the interactions between the drug (e.g., DHM) and the HME polymer. For example, the drug (e.g., DHM) can be substantially soluble in the molten polymer phase, which can include one or more excipient(s) and/or plasticizers, such that upon cooling and solidification, that drug is prevented from substantially crystalizing. Capturing the drug (e.g., DHM) in an amorphous, or non-crystalline-associated state (which can be a high-energy state), can result in a higher dissolution level or a supersaturation level, when dissolved in vitro or in vivo. Thermodynamic reasons for this increase in solubility have been discussed by Hu, Johnson & Williams.[36]

Commercially supplied pure DHM can be entirely (100%) or nearly entirely crystalline.

The crystallinity of the DHM in the hot-melt extruded (HME) formulation can be qualitatively assessed or quantitatively measured by techniques, such as polarized light microscopy (PLM), differential scanning calorimetry (DCS), and powder X-ray diffraction (P-XRD). The DHM in the hot-melt extruded (HME) formulation can have a crystallinity of less than or equal to 90%, 80%, 60%, 50%, 40%, 30%, 20%, 25%, 20%, 15%, 10%, 7%, 5%, 3%, 2%, or 1%. The DHM in the hot melt extruded formulation (extrudate) can be amorphous.

Dissolution Kinetics Studies

In an embodiment, the DHM in the hot melt extrusion formulation (extrudate) does not dissolve in and/or is not solubilized by an aqueous solution having a pH of at most (i.e., less than or equal to) 4.8, 4.5, 4, 3.5, 3.2, 3, 2.7, 2.5, 2.3, 2, 1.8, 1.5, or 1. The chyme that is expelled by the stomach, through the pyloric valve, has a pH of approximately 2. Gastric juices lead to material in the stomach having a pH in the range of from 1.5 to 3.5, and this low pH in the stomach and the enzymes active in the stomach at this low pH may result in degradation of DHM and quenching of DHM activity.

In an embodiment, the DHM in the hot-melt extruded (HME) formulation dissolves in and/or is solubilized by water (pH of 7) and/or an aqueous solution having a pH of at least (i.e., greater than or equal to) 5, 5.3, 5.5, 5.8, 6, 6.2, 6.5, 6.7, 7, 7.2, or 7.5. Bile released into the duodenum and/or pancreatic secretions of sodium bicarbonate increase the pH of the chyme. For example, the pH of chyme and material in the intestine (bowel) can range from 5.5 to 7, for example, can be 7. The dissolution and/or solubilization of the DHM in the hot melt extruded formulation in the intestine, for example, the small intestine, can result in the DHM being absorbed by the wall of the intestine, for example, the wall of the small intestine, and into the blood.

For example, hydroxypropyl methyl cellulose acetate succinate (HPMCAS) is insoluble in an aqueous solution of acidic (low) pH, but is soluble in an aqueous solution of neutral or alkaline (high) pH. Therefore, a hot-melt extruded (HME) formulation including HPMCAS and DHM can retain the DHM at an acidic (low) pH, e.g., a pH of 3.5 or less, but release the DHM at a neutral or alkaline (high) pH, e.g., a pH of 7 or greater.

A pH buffering agent can be included in such a hot-melt extruded (HME) formulation.

Inclusion of an acidic component in such a hot-melt extruded (HME) formulation, such as an acidic pH buffering agent (i.e., a buffering agent that maintains an acidic pH, a pH of less than 7), e.g., citric acid or a citrate salt (e.g., a sodium citrate, a potassium citrate, calcium citrate, and/or combinations), can stabilize an aqueous solution formed with the hot-melt extruded (HME) formulation, so that the DHM is not released into the aqueous solution or so that the release of the DHM into the aqueous solution is delayed.

The polymer matrix material can be selected, so that it is moderately soluble (e.g., from 0.01 g/100 mL to 3 g/100 mL, or from 0.1 g/100 mL to 1 g/100 mL) in water. Moderate solubility in water allows the polymer matrix material to dissolve in the body of an organism and release the DHM.

The dissolution and release kinetics of DHM are studied under different conditions; three protocols are described as follows.[37]

Release Kinetics in Vitro: Simulated gastric fluid (FaSSGF) and intestinal fluids (FaSSIF and FeSSIF) are prepared according to the manufacturer's instructions. Dissolution tests are performed with hot-melt extruded (HME) DHM-containing powders or tablets with the appropriate controls.

Release under Gastric Conditions: DHM-containing hot melt extruded (HME) powder samples are suspended in prewarmed FaSSGF (37° C.) to achieve a drug (DHM) concentration of roughly 10-100× the previously determined equilibrium solubility in the FaSSGF fluid (e.g., 75 g/mL) by pipetting up and down vigorously multiple times. The samples are incubated for the duration of the study (e.g., 30 min) at 37° C. (NesLab RTE-111 bath circulator, Thermo Fisher Scientific, Waltham, MA) without agitation to mimic physiological gastric conditions and transition time in the stomach. Aliquots can be taken, for example, at 1, 5, 10, 15, 30, 60, 120, and 360 min. To analyze the free DHM concentration, each aliquot can be centrifuged at 28000 g for 5 min to pellet suspended particles. The supernatant is frozen and lyophilized; the remaining solids are reconstituted in, for example, 2:8 THF (tetrahydrofuran):acetonitrile to dissolve DHM and precipitate out lipids and salts from the release media. The samples are then diluted as appropriate to fall within the detection range and analyzed by high-performance liquid chromatography (HPLC), with the mobile phase as 80:20 $H_2O$:acetonitrile (each with 0.05% trifluoroacetic acid), and with detection with UV-Vis at 290 nm. The concentration of DHM is then calculated based on a calibration curve.

Release under Intestinal Conditions: DHM-containing hot melt extruded (HME) powder samples are suspended in prewarmed (37° C.) Fed State Simulated Intestinal Fluid (FeSSIF) or Fasted State Simulated Intestinal Fluid (FaSSIF) to achieve a drug (DHM) concentration of roughly 10-100× the previously determined equilibrium solubility in the FeSSIF or FaSSIF fluid by pipetting up and down vigorously multiple times. The equilibrium solubility of crystalline DHM in FeSSIF was measured to be about 140 g/mL, and the equilibrium solubility of crystalline DHM in FaSSIF is about 50 g/mL. Aliquots are taken at, for example, 1, 5, 10, 15, 30, 60, 120, and 360 min and centrifuged at, for example, 28000 g for 10 min. The supernatant is frozen and lyophilized; the remaining solids are reconstituted in, for example, 2:8 THF (tetrahydrofuran):acetonitrile to dissolve DHM and precipitate out lipids and salts from the release media. The samples are then diluted as appropriate to fall within the detection range and analyzed by HPLC, with the mobile phase as 80:20 $H_2O$:acetonitrile (each with 0.05% trifluoroacetic acid), and with detection with UV-Vis at 290 nm. The concentration of DHM is then calculated based on a calibration curve.

FaSSIF is a biorelevant intestinal media representing the fasted state intestinal fluid, and FeSSIF is another biorelevant intestinal media representing the fed state intestine fluid. FaSSIF and FeSSIF have different compositions. For example, components of FaSSIF include 3 mM taurocholate, 0.75 mM phospholipids, 148 mM sodium, 106 mM chloride, and 29 mM phosphate, while components of FeSSIF include 15 mM taurocholate, 3.75 mM phospholipids, 319 mM sodium, 203 mM chloride, and 144 mM acetic acid. In in vivo tests, the presence of food changes the pH and composition of fats and surfactants in the intestinal fluid. FaSSIF has a higher pH (6.5) than FeSSIF (5.0) and has lower levels of fat.

The intestine can be the site of absorption for oral dosage forms, thus understanding the solubility of a drug or active ingredient in the intestinal fluid can be important.

For example, the dissolution kinetics of DHM in a hot-melt extruded (HME) formulation in an embodiment of the present invention in in vitro dissolution tests in simulated fasted state fluid can be increased by 5%, 10%, 15%, 20%, 30%, 40%, 50%, 60%, 100%, or 250% after 15 minutes over that of pure DHM.

For example, the dissolution kinetics of DHM in a hot-melt extruded (HME) formulation in an embodiment of the present invention in in vitro dissolution tests in simulated fed state fluid can be increased by 5%, 10%, 15%, 20%, 30%, 40%, 50%, 60%, 100%, or 250% after 15 minutes over that of pure DHM.

For example, the dissolution kinetics of DHM in a hot-melt extruded (HME) formulation in an embodiment of the present invention in in vitro dissolution tests in simulated fasted state fluid can be increased by 5%, 10%, 15%, 20%, 30%, 40%, 50%, 60%, 100%, or 250% after 30 minutes over that of pure DHM.

For example, the dissolution kinetics of DHM in a hot-melt extruded (HME) formulation in an embodiment of the present invention in in vitro dissolution tests in simulated fed state fluid can be increased by 5%, 10%, 15%, 20%, 30%, 40%, 50%, 60%, 100%, or 250% after 30 minutes over that of pure DHM.

For example, the dissolution kinetics of DHM in a hot-melt extruded (HME) formulation in an embodiment of the present invention in in vitro dissolution tests in simulated fasted state fluid can be increased by 5%, 10%, 15%, 20%, 30%, 40%, 50%, 60%, 100%, or 250% after 60 minutes over that of pure DHM.

For example, the dissolution kinetics of DHM in a hot-melt extruded (HME) formulation in an embodiment of the present invention in in vitro dissolution tests in simulated fed state fluid can be increased by 5%, 10%, 15%, 20%, 30%, 40%, 50%, 60%, 100%, or 250% after 60 minutes over that of pure DHM.

For example, the dissolution kinetics of DHM in a hot-melt extruded (HME) formulation in an embodiment of the present invention in in vitro dissolution tests in simulated fasted state fluid can be increased by 5%, 10%, 15%, 20%, 30%, 40%, 50%, 60%, 100%, or 250% after 120 minutes over that of pure DHM.

For example, the dissolution kinetics of DHM in a hot-melt extruded (HME) formulation in an embodiment of the present invention in in vitro dissolution tests in simulated fed state fluid can be increased by 5%, 10%, 15%, 20%, 30%, 40%, 50%, 60%, 100%, or 250% after 120 minutes over that of pure DHM.

For example, the dissolution kinetics of DHM in a hot-melt extruded (HME) formulation in an embodiment of the present invention in in vitro dissolution tests in simulated fasted state fluid can be increased by 5%, 10%, 15%, 20%, 30%, 40%, 50%, 60%, 100%, or 250% after 360 minutes over that of pure DHM.

For example, the dissolution kinetics of DHM in a hot-melt extruded (HME) formulation in an embodiment of the present invention in in vitro dissolution tests in simulated fed state fluid can be increased by 5%, 10%, 15%, 20%, 30%, 40%, 50%, 60%, 100%, or 250% after 360 minutes over that of pure DHM.

Animal PK Studies

DHM-containing samples (e.g., hot-melt extruded (HME) formulations in an embodiment of the present invention) can be administered (e.g., through oral gavage) to an animal (e.g., a rat or a mouse) at 10 mg DHM/kg body weight, 75 mg DHM/kg body weight, or another dosage in an in vivo study, and a pharmacokinetic study can be carried out to evaluate animal pharmacokinetics. The plasma concentration of DHM can be determined, for example, using a Waters Acquity ultra performance liquid chromatography system equipped with an electrospray ionization mass spectrometry system (Waters, Milford, MA), in accordance with a previous report [38], or an equivalent analytical analysis system.

An animal dosed with a hot melt extrusion formulation containing DHM according to the present invention can show increased blood maximum concentrations, relative to dosing with pure DHM powder, of 5%, 10%, 15%, 20%, 30%, 40%, 50%, 60%, 100%, 250%. The area under the curve (AUC) for 24 hours can be increased by 5%, 10%, 15%, 20%, 30%, 40%, 50%, 60%, 100%, 250% over the value associated with dosing with pure DHM powder.

Several nonlimiting Aspects of the invention are set forth below.

Aspect 1. A dihydromyricetin (DHM) formulation, comprising:
  dihydromyricetin (DHM) and
  a matrix material,
  wherein the DHM is dispersed within the matrix material and
  wherein the matrix material is a solid.

Aspect 2. The DHM formulation of Aspect 1, wherein the matrix material comprises a polymeric matrix material.

Aspect 3. The DHM formulation of any one of Aspects 1 through 2, wherein the matrix material comprises cellulose and/or a cellulose derivative.

Aspect 4. The DHM formulation of any one of Aspects 1 through 3, wherein the matrix material comprises hydroxypropyl methyl cellulose (HPMC).

Aspect 5. The DHM formulation of any one of Aspects 1 through 4, wherein the matrix material comprises a material selected from the group consisting of cellulose ester, cellulose acrylate, methyl cellulose, ethyl cellulose, hydroxyethyl cellulose, hydroxypropylcellulose (HPC), hydroxypropyl methylcellulose propionate succinate, hydroxypropyl methyl cellulose phthalate (HPMCP), hydroxypropyl methyl cellulose acetate succinate (HPMCAS), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), carboxymethylcellulose, carboxymethylcellulose salt, sodium carboxymethylcellulose, a cellulose polymer, and combinations.

Aspect 6. The DHM formulation of any one of Aspects 1 through 5, wherein the matrix material comprises polyethylene oxide (PEO).

Aspect 7. The DHM formulation of any one of Aspects 1 through 6, wherein the matrix material comprises a material selected from the group consisting of polyoxyethylene-polyoxypropylene block copolymers (also referred to as poloxamers), polyoxyethylene alkyl ethers, polyoxyethylene castor oils, a low molecular-weight oligomer of polyethylene glycol, an ethylene glycol-vinyl glycol copolymer, polyoxyethylene castor oils, ethoxylated castor oil, polyoxyl hydrogenated castor oil, polyoxyl 40 hydrogenated castor oil, polyethoxylated sorbitan, polyoxyethylene sorbitan monooleate, and combinations.

Aspect 8. The DHM formulation of any one of Aspects 1 through 7, wherein the matrix material comprises a material selected from the group consisting of polyvinyl pyrrolidone (PVP) and poly(vinyl pyrrolidone-co-vinyl acetate) (PVP-VA).

Aspect 9. The DHM formulation of any one of Aspects 1 through 8, wherein the matrix material comprises a material selected from the group consisting of poly(methyl methacrylate) (PMMA), low molecular weight poly(methyl methacrylate), polymethacrylate, methacrylic acid copolymers, polymethacrylate derivatives, poly(methacrylic acid-co-methyl methacrylate) 1:1, poly(methacrylic acid-co-methyl methacrylate) 1:2, poly(methacrylic acid-co-ethyl acrylate) 1:1, and combinations.

Aspect 10. The DHM formulation of any one of Aspects 1 through 9, wherein the matrix material comprises a material selected from the group consisting of polycaprolactam, polycaprolactone (PCL), polylactic acid (PLA), polyglycolic acid (PGA), poly(lactic-glycolic acid) (PLGA), and combinations.

Aspect 11. The DHM formulation of any one of Aspects 1 through 10, wherein the matrix material comprises a material selected from the group consisting of a wax, low melting point waxes such as carnauba wax, starch, starch derivatives, sugars, sugar alcohols, leucine, lipids, a polyol, a polyether, fructose, glucose, lactose, mannitol, trehalose, sucrose, raffinose, maltitol, lactitol, sorbitol, xylitol, erythritol, xylose, acorbose, melezitose, galactose, melibrose, isomaltose, a natural sugar extracts, malt beet sugar, corn sugar, high-fructose corn syrup, a sugar oligomers, polydextrose and dextrans with molecular weights less than 10,000 Daltons, a polyol, glycerol, sorbitol, ethylene glycol, propylene glycol, butanediol, polymeric derivatives of vitamin E, poly(propylene), and combinations.

Aspect 12. The DHM formulation of any one of Aspects 1 through 11, further comprising a plasticizer.

Aspect 13. The DHM formulation of Aspect 12, wherein the plasticizer comprises a plasticizer selected from the group consisting of low molecular weight polyols having aliphatic hydroxyls, poly(propylene glycol), low molecular weight poly(ethylene oxide) (e.g., having an average molecular weight of less than about 500,000 Da), and poly(ethylene glycol), D-alpha tocopheryl PEG 1000 succinate (TPGS), low molecular-weight polyethylene glycol, propylene glycol, 1,2-butylene glycol, 2,3-butylene glycol, triethylene glycol, tetraethylene glycol and other poly(ethylene glycol) compounds, mono propylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, allyl glycolate, and combinations.

Aspect 14. The DHM formulation of any one of Aspects 12 and 13, wherein the plasticizer comprises a plasticizer selected from the group consisting of triacetin, vitamin E, pressurized $CO_2$, citrate ester, triethyl citrate, acetyl triethyl citrate, tributyl citrate, and combinations.

Aspect 15. The DHM formulation of any one of Aspects 12 through 14, wherein the plasticizer comprises a plasticizer selected from the group consisting of a low molecular weight polymer, an oligomer, a copolymers, an oil, a small organic molecule, an ester-type plasticizer, a multi-block polymer, a single block polymer, a molecular surfactant, styrene, a glycol, a glycol ether, and combinations.

Aspect 16. The DHM formulation of any one of Aspects 1 through 15, further comprising a permeabilizer.

Aspect 17. The DHM formulation of Aspect 16, wherein the permeabilizer comprises caprylic acid, a caprylate salt, and/or sodium caprylate.

Aspect 18. The DHM formulation of any one of Aspects 16 and 17, wherein the permeabilizer comprises a permeabilizer selected from the group consisting of a fatty acid, a saturated fatty acid, and/or a fatty acid complexed with a cation, such as a metal cation, a metal divalent cation, a magnesium divalent cation, a calcium divalent cation, a zinc divalent cation, an iron divalent cation, a metal trivalent cation, an iron trivalent cation, a fatty acid salt, a fatty acid metallic soap, and combinations.

Aspect 19. The DHM formulation of any one of Aspects 1 through 18, further comprising a coactive.

Aspect 20. The DHM formulation of Aspect 19, wherein the coactive comprises an antioxidant.

Aspect 21. The DHM formulation of any one of Aspects 19 and 20, wherein the coactive is glutathione.

Aspect 22. The DHM formulation of any one of Aspects 19 through 21, wherein the coactive is L-cysteine.

Aspect 23. The DHM formulation of any one of Aspects 19 through 22, wherein the coactive is selected from the group consisting of N-acetyl cysteine (NAC), Prickly Pear extract, Milk Thistle, ginger root, vitamin B, vitamin C, vitamin E, and combinations.

Aspect 24. The DHM formulation of any one of Aspects 19 through 23, wherein the coactive comprises an electrolyte and/or a sugar.

Aspect 25. The DHM formulation of any one of Aspects 1 through 24, further comprising a pH buffering agent.

Aspect 26. The DHM formulation of Aspect 25, wherein the pH buffering agent is an acidic pH buffering agent.

Aspect 27. The DHM formulation of Aspect 26, wherein the acidic pH buffering agent comprises citric acid, a citrate salt, a sodium citrate, a potassium citrate, calcium citrate, and/or combinations.

Aspect 28. The DHM formulation of any one of Aspects 1 through 27, wherein the DHM is not solubilized or dissolved by an aqueous solution having a pH of at most 3.5.

Aspect 29. The DHM formulation of any one of Aspects 1 through 28, wherein the DHM is not solubilized or dissolved by an aqueous solution having a pH of at most 2.

Aspect 30. The DHM formulation of any one of Aspects 1 through 29, wherein the DHM is solubilized or dissolved by an aqueous solution having a pH of at least 5.5.

Aspect 31. The DHM formulation of any one of Aspects 1 through 29, wherein the DHM is solubilized or dissolved by water or an aqueous solution having a pH of at least 7.

Aspect 32. The DHM formulation of any one of Aspects 1 through 31, wherein the DHM comprises at least 5 wt % of the powder.

Aspect 33. The DHM formulation of any one of Aspects 1 through 31, wherein the DHM comprises at least 20 wt % of the powder.

Aspect 34. The DHM formulation of any one of Aspects 1 through 31, wherein the DHM comprises at least 40 wt % of the powder.

Aspect 35. The DHM formulation of any one of Aspects 1 through 31, wherein the DHM comprises at least 55 wt % of the powder.

Aspect 36. The DHM formulation of any one of Aspects 1 through 35, wherein the crystallinity of the DHM is at most 20% Aspect 37. The DHM formulation of any one of Aspects 1 through 35, wherein the crystallinity of the DHM is at most 10%.

Aspect 38. The DHM formulation of any one of Aspects 1 through 35, wherein the crystallinity of the DHM is at most 5%.

Aspect 39. The DHM formulation of any one of Aspects 1 through 35, wherein the crystallinity of the DHM is at most 2%.

Aspect 40. The DHM formulation of any one of Aspects 1 through 35, wherein the DHM is amorphous.

Aspect 41. The DHM formulation of any one of Aspects 1 through 40, wherein the DHM formulation is homogeneous and/or molecularly dispersed.

Aspect 42. A dosage form, comprising
the DHM formulation of any one of Aspects 1 through 41, and
an enteric coating that encapsulates the DHM formulation.

Aspect 43. The dosage form of Aspect 42, wherein the enteric coating is a polymeric coating.

Aspect 44. The dosage form of Aspect 42, wherein the enteric coating is a methacrylate copolymer coating.

Aspect 45. The dosage form of any one of Aspects 42 through 44, wherein the dosage form is a capsule, tablet, or pill.

Aspect 46. A dosage form, comprising
the DHM formulation of any one of Aspects 1 through 41 in a powder form, and
an aqueous liquid,
wherein the DHM formulation in a powder form is mixed with or suspended in the liquid.

Aspect 47. A dosage form, comprising
the DHM formulation of any one of Aspects 1 through 41 in a powder form, and
a gel,
wherein the DHM formulation in a powder form is mixed with or suspended in the gel.

Aspect 48. The DHM formulation of Aspect 1,
wherein the matrix material is polyethylene oxide (PEO), and
wherein the DHM comprises at least 5 wt % of the DHM formulation.

Aspect 49. The DHM formulation of Aspect 1,
wherein the matrix material is hydroxypropyl methylcellulose (HPMC), and
wherein the DHM comprises at least 5 wt % of the DHM formulation.

Aspect 50. A method for forming a dihydromyricetin (DHM) formulation of any one of Aspects 1 through 41, Aspect 48, and Aspect 49 or the dosage form according to any one of Aspects 42 through 47, comprising:
mixing the dihydromyricetin (DHM) and the matrix material to form a compounding mixture;
processing the compounding mixture in an extruder to form an extrudate; and
collecting the extrudate as the dihydromyricetin (DHM) formulation.

Aspect 51. The method of Aspect 50, further comprising grinding the extrudate into a powder.

Aspect 52. The method of Aspect 51, further comprising filling the powder into a capsule or pressing the powder into a tablet.

Aspect 53. The method of Aspect 50, comprising,
mixing the dihydromyricetin (DHM) and polyethylene oxide (PEO) as the matrix material to form the compounding mixture;
wherein the weight ratio of DHM to PEO is 5:95,
processing the compounding mixture in the extruder to form the extrudate; and
collecting the extrudate as the dihydromyricetin (DHM) formulation.

Aspect 54. The method of Aspect 50, comprising,
mixing the dihydromyricetin (DHM) and hydroxypropyl methylcellulose (HPMC) as the matrix material to form the compounding mixture;
wherein the weight ratio of DHM to HPMC is 5:95,
processing the compounding mixture in the extruder to form the extrudate; and
collecting the extrudate as the dihydromyricetin (DHM) formulation.

Aspect 55. The dihydromyricetin (DHM) formulation of any one of Aspects 1 through 41, Aspect 48, and Aspect 49 or the dosage form according to any one of Aspects 42 through 47 for use as a medicament.

Aspect 56. The dihydromyricetin (DHM) formulation of any one of Aspects 1 through 41, Aspect 48, and Aspect 49 or the dosage form according to any one of Aspects 42 through 47 for use in reducing hangover symptoms.

Aspect 57. The dihydromyricetin (DHM) formulation of any one of Aspects 1 through 41, Aspect 48, and Aspect 49 or the dosage form according to any one of Aspects 42 through 47 for use in preventing an alcohol use disorder.

Aspect 58. The dihydromyricetin (DHM) formulation of any one of Aspects 1 through 41, Aspect 48, and Aspect 49 or the dosage form according to any one of Aspects 42 through 47 for use in preventing alcoholism.

Aspect 59. The dihydromyricetin (DHM) formulation of any one of Aspects 1 through 41, Aspect 48, and Aspect 49 or the dosage form according to any one of Aspects 42 through 47 for use in treating an alcohol use disorder.

Aspect 60. The dihydromyricetin (DHM) formulation of any one of Aspects 1 through 41, Aspect 48, and Aspect 49 or the dosage form according to any one of Aspects 42 through 47 for use in treating alcoholism.

Aspect 61. The dihydromyricetin (DHM) formulation of any one of Aspects 1 through 41, Aspect 48, and Aspect 49 or the dosage form according to any one of Aspects 42 through 47 for use in treating an alcohol overdose.

Aspect 62. The dihydromyricetin (DHM) formulation of any one of Aspects 1 through 41, Aspect 48, and Aspect 49 or the dosage form according to any one of Aspects 42 through 47 for use in increasing antioxidant capacity.

Aspect 63. The dihydromyricetin (DHM) formulation of any one of Aspects 1 through 41, Aspect 48, and Aspect 49 or the dosage form according to any one of Aspects 42 through 47 for use in neuroprotection.

Aspect 64. The dihydromyricetin (DHM) formulation of any one of Aspects 1 through 41, Aspect 48, and Aspect 49 or the dosage form according to any one of Aspects 42 through 47 for use in preventing Alzheimer's disease.

Aspect 65. The dihydromyricetin (DHM) formulation of any one of Aspects 1 through 41, Aspect 48, and Aspect 49 or the dosage form according to any one of Aspects 42 through 47 for use in treating Alzheimer's disease.

Aspect 66. The dihydromyricetin (DHM) formulation of any one of Aspects 1 through 41, Aspect 48, and Aspect 49 or the dosage form according to any one of Aspects 42 through 47 for use in inhibiting inflammation.

Aspect 67. The dihydromyricetin (DHM) formulation of any one of Aspects 1 through 41, Aspect 48, and Aspect 49 or the dosage form according to any one of Aspects 42 through 47 for use in protection of the kidney.

Aspect 68. The dihydromyricetin (DHM) formulation of any one of Aspects 1 through 41, Aspect 48, and Aspect 49 or the dosage form according to any one of Aspects 42 through 47 for use in protection of the liver.

Aspect 69. The dihydromyricetin (DHM) formulation of any one of Aspects 1 through 41, Aspect 48, and Aspect 49 or the dosage form according to any one of Aspects 42 through 47 for use in preventing or treating cancer.

Aspect 70. The dihydromyricetin (DHM) formulation of any one of Aspects 1 through 41, Aspect 48, and Aspect 49 or the dosage form according to any one of Aspects 42 through 47 for use in ameliorating a metabolic disorder.

Aspect 71. The dihydromyricetin (DHM) formulation of any one of Aspects 1 through 41, Aspect 48, and Aspect 49 or the dosage form according to any one of Aspects 42 through 47 for use in preventing diabetes.

Aspect 72. The dihydromyricetin (DHM) formulation of any one of Aspects 1 through 41, Aspect 48, and Aspect 49 or the dosage form according to any one of Aspects 42 through 47 for use in treating diabetes.

Aspect 73. The dihydromyricetin (DHM) formulation of any one of Aspects 1 through 41, Aspect 48, and Aspect 49 or the dosage form according to any one of Aspects 42 through 47 for use in treating a bacterial infection.

Aspect 74. Use of the dihydromyricetin (DHM) formulation of any one of Aspects 1 through 41, Aspect 48, and Aspect 49 in the manufacture of a medicament for reducing hangover symptoms.

Aspect 75. Use of the dihydromyricetin (DHM) formulation of any one of Aspects 1 through 41, Aspect 48, and Aspect 49 in the manufacture of a medicament for preventing an alcohol use disorder, preventing alcoholism, treating an alcohol use disorder, treating alcoholism, and/or treating an alcohol overdose.

Aspect 76. Use of the dihydromyricetin (DHM) formulation of any one of Aspects 1 through 41, Aspect 48, and Aspect 49 in the manufacture of a medicament for neuroprotection, preventing Alzheimer's disease, and/or treating Alzheimer's disease.

Aspect 77. Use of the dihydromyricetin (DHM) formulation of any one of Aspects 1 through 41, Aspect 48, and Aspect 49 in the manufacture of a medicament for ameliorating a metabolic disorder, preventing diabetes, and/or treating diabetes.

Aspect 78. Use of the dihydromyricetin (DHM) formulation of any one of Aspects 1 through 41, Aspect 48, and Aspect 49 in the manufacture of a medicament for increasing antioxidant capacity, inhibiting inflammation, protecting the kidney, protecting the liver, preventing and/or treating cancer, and/or treating a bacterial infection.

Aspect 79. The DHM formulation of any one of Aspects 1 through 41, Aspect 48, and Aspect 49, so that mixing of the DHM formulation with a solvent results in a concentration of DHM dissolved in the solvent that is at least 20%, 50%, 70%, 100%, 200%, 400%, or 900% greater than the equilibrium concentration of crystalline DHM dissolved in the solvent.

Aspect 80. The DHM formulation of Aspect 79, wherein the solvent is an aqueous solvent.

Aspect 81. The DHM formulation of Aspect 79, wherein the solvent is an aqueous solvent of pH in the range of 4.5 to 7.0.

Aspect 82. The DHM formulation of Aspect 79, wherein the solvent is an aqueous solvent of pH in the range of 4.5 to 7.0 and comprising sodium at a concentration of from 100 mM to 400 mM.

Aspect 83. The DHM formulation of Aspect 79, wherein the solvent is an aqueous solvent of pH in the range of 4.5 to 7.0 and comprising sodium at a concentration of from 100 mM to 400 mM and a surfactant at a concentration of from 0.01 wt % to 2 wt %.

Aspect 84. The DHM formulation of Aspect 79, wherein the solvent is an aqueous solvent of pH in the range of 4.5 to 7.0 and comprising sodium at a concentration of from 100 mM to 400 mM and a nonionic surfactant at a concentration of from 0.05 wt % to 1.5 wt %.

Aspect 85. The DHM formulation of Aspect 79, wherein the solvent is fed state simulated intestinal fluid (FeSSIF).

Aspect 86. The DHM formulation of Aspect 79, wherein the solvent is fed state simulated intestinal fluid (FeSSIF) further comprising polysorbate at a concentration of about 1 wt %.

Aspect 87. The DHM formulation of Aspect 79, wherein the solvent is fasted state simulated intestinal fluid (FaSSIF).

Aspect 88. The DHM formulation of Aspect 79, wherein the solvent is fasted state simulated intestinal fluid (FaSSIF) further comprising polysorbate at a concentration of about 1 wt %.

EXAMPLES

The following example(s) provide descriptions of embodiments of the invention. It is recognized that departures from the disclosed embodiment may be made within the scope of the invention and that obvious modifications will occur to a person skilled in the art. The claims and specification should not be construed to unduly narrow the full scope of protection to which the invention is entitled.

Example 1: Preparation of a DHM—Poly(Ethylene Oxide) Hot-Melt Extruded (HME) Formulation An amount of dihydromyricetin (DHM) sufficient to provide an effective amount of the formulation may be mixed with a known amount of polyethylene oxide (PEO) polymer. The weight ratio of DHM to polymer may be about 5:95. The mixture may then be placed into an extruder hopper. The extruder used should include a solids-conveying mechanism (e.g., a screw or twin screws) that extends from the hopper through a heating zone to the extrusion die. The mixture is passed through the heated extruder at a temperature range which may be from about 100° C. to about 140°

C., as set by the temperature setting of the extruder heating zone, so that melting or softening of the PEO occurs. Upon exiting the die, the extrudate (PEO/DHM) may be chopped to the desired length. The extrudate may then be, for example, ground to a powder and filled into a capsule or pressed into a tablet.

Example 2: Preparation of a DHM—Cellulosic Hot-Melt Extruded (HME) Formulation

An amount of dihydromyricetin (DHM) sufficient to provide an effective amount of the formulation may be mixed with a known amount of cellulose-derived AFFINISOL™ HPMC HME hydroxypropyl methylcellulose (HPMC) polymer of low to medium molecular weight. The weight ratio of DHM to polymer may be about 5:95. The mixture may then be placed into an extruder hopper. The extruder to be used should include a solids-conveying mechanism (e.g., a screw or twin screws) that extends from the hopper through a heating zone to the extrusion die. The mixture is passed through the heated extruder at a temperature range which may be from about 100° C. to about 155° C., as set by the temperature setting of the extruder heating zone, so that the polymer is sufficiently melted or softened. Upon exiting the die, the extrudate (HPMC/DHM) may be chopped to the desired length. The extrudate may then be, for example, ground to a powder, filled into a capsule, or pressed into a tablet.

Example 3: Preparation of a DHM—Poly(Vinylpyrrolidone-Co-Vinyl Acetate) (PVP-VA) Hot-Melt Extruded (HME) Formulation An amount of dihydromyricetin (DHM) sufficient to provide an effective amount of the formulation was mixed with a known amount of poly(vinylpyrrolidone-co-vinyl acetate) (PVP-VA). The PVP-VA used was BASF Kollidon VA 64, which is an amorphous copolymer having 60% vinylpyrrolidone and 40% vinyl acetate, a molecular weight of about 45,000 g/mol, and a glass-transition temperature (Tg) measured to be 109° C. The DHM and PVP-VA were mixed and ground by hand in a mortar and pestle to form a physical mixture that was fed to an extruder. A HAAKE Mini-Lab II extruder having a chamber volume of 7 cm$^3$, counter-rotating twin screws, and an internal recirculation channel was used. Approximately 5 g of the physical mixture of DHM and PVP-VA was loaded into the extruder. The mixture was passed through the heated extruder at about 160° C., with the extruder operated at 30-50 rpm. Approximately 5 min loading time, 5 min recirculation time, and 5 min unloading time were used. The extrudate was then collected as the dihydromyricetin (DHM) formulation.

In the exemplary extrudate produced, the drug (DHM) loading in the extrudate was 20 wt %, i.e., the weight ratio of DHM:PVP-VA was 20:80. (For example, in other cases, the weight ratio of DHM to PVP-VA may be about 5:95, 10:90, 30:70, 40:60, 50:50, 60:40, or 80:20.)

The DHM/PVP-VA (20/80) extrudate from this hot melt extrusion (HME) was darker brown and uniform in color and somewhat opaque, indicating that the DHM was uniformly dispersed in the extrudate. The glass-transition temperature (Tg) of this DHM/PVP-VA (20/80) HME extrudate was 126° C. The PVP-VA in the DHM/PVP-VA (20/80) extrudate was amorphous.

In comparison, extruded PVP-VA polymer (without DHM) was lighter brown in color and more translucent. The Tg of this extruded PVP-VA polymer was measured to be 108° C., the same as the bulk PVP-VA (BASF Kollidon VA64) copolymer, indicating that extrusion did not change the Tg of the polymer. The PVP-VA in the extrudate was amorphous.

The melting temperature (point) Tm of DHM is approximately 240° C.-256° C., for example, about 240° C. Thus, the operating temperature of the extruder, about 160° C. was less than the melting temperature of the DHM. Without being bound by theory, the DHM was thought to have dissolved into the molten PVP-VA polymer in the extruder.

The Tg of DHM is inferred to be less than 120° C. That is, a spray dried dispersion (SDD) of DHM and hydroxypropyl methylcellulose acetate succinate (HPMCAS) exhibited an intermediate Tg less than the Tg of HPMCAS (~120° C.), so that the Tg of DHM is inferred to be less than the Tg of HPMCAS.

Thus, the Tg of the DHM/PVP-VA (20/80) HME extrudate (126° C.) was greater than the Tg of the DHM (less than 120° C.) and was greater than the Tg of the PVP-VA matrix (about 108° C.).

Example 4: Characterization of DHM Release from a DHM—Matrix Hot-Melt Extruded (HME) Formulation In vitro release data may be obtained to allow comparison of the concentration of DHM in a liquid yielded by starting crystalline DHM material with the concentration of DHM in a liquid yielded by a DHM—matrix HME formulation over a time period, such as a 6-hour time period with sampling timepoints at 1, 5, 10, 15, 30, 60, 120, and 360 minutes.

For example, the release study may be performed in fed state simulated intestinal fluid (FeSSIF), with or without 1% v/v Tween 20 (Polysorbate 20) having been added. The fluid may be maintained at a temperature of 37° C. for the duration of the experiment. For each study, the starting crystalline DHM material or the HME formulation may be loaded into a separate volume of prepared FeSSIF fluid at a concentration substantially greater than the equilibrium solubility of DHM in FeSSIF (140 g/mL). For example, the starting crystalline DHM material or the HME formulation may be loaded into the prepared FeSSIF fluid at a DHM concentration of 1400 g/mL, 10 times the equilibrium solubility of crystalline DHM in FeSSIF, or at a DHM concentration of 7 mg/mL, 50 times the equilibrium solubility of DHM in FeSSIF. (The excess DHM loaded into the release media enables detection and quantitation of potentially supersaturated dissolved DHM concentrations that a given formulation may provide.) At the completion of the release studies, the HME formulation may be found to produce a supersaturated DHM concentration that is greater than that of the crystalline DHM.

Such release studies may establish that the HME formulation will release a concentration of dissolved DHM into a patient's intestine that is greater than the concentration of dissolved DHM released by crystalline DHM. The greater concentration of dissolved DHM released into the patient's intestine may result in the HME formulation promoting uptake of DHM into the overall system (body) of the patient that is greater than the DHM uptake when crystalline DHM is administered, by way of an increased concentration driving force of the DHM across the membrane of the intestine.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Powell, B. A. R., COMPOSITIONS AND METHODS FOR PREVENTING AND RECOVERY FROM DETRIMENTAL EFFECTS OF ALCOHOL CONSUMPTION, U.S. Pat. No. 9,603,830, (Mar. 28, 2017), THRIVEPLUS LLC: USA.
2. Shen, Y., et al., *Dihydromyricetin As a Novel Anti-Alcohol Intoxication Medication.* The Journal of Neuroscience, 2012. 32(1): p. 390-401.
3. Breitenbach, J., *Melt extrusion: from process to drug delivery technology.* European Journal of Pharmaceutics and Biopharmaceutics, 2002. 54(2): p. 107-117.
4. Chokshi, R. and H. Zia, *Hot-melt extrusion technique: a review.* Iranian Journal of Pharmaceutical Research, 2010: p. 3-16.
5. Crowley, M. M., et al., *Pharmaceutical applications of hot-melt extrusion: part I.* Drug development and industrial pharmacy, 2007. 33(9): p. 909-926.
6. Maniruzzaman, M., et al., *A review of hot-melt extrusion: process technology to pharmaceutical products.* ISRN pharmaceutics, 2012. 2012.
7. Patil, H., R. V. Tiwari, and M. A. Repka, *Hot-Melt Extrusion: from Theory to Application in Pharmaceutical Formulation.* AAPS PharmSciTech, 2015. 17(1): p. 20-42.
8. Liang, J., R. Olsen, and I. Spigelman, Methods of treating alcohol intoxication, alcohol use disorders, and alcohol abuse which comprise the administration of dihydromyricetin, in Google Patents. 2012, The Regents of the University of California.
9. Thomson, J. E., J. John V. Landry, and M. W. Zembal, HOT-MELT EXTRUSION COATING OF RANDOM COPOLYMER OF ETHYLENE AND MONO-CARBOXYLIC ACID, in Google Patents. 1966, The Dow Chemical Company: USA.
10. Schippers, H. and Remscheid-Lennep, APPARATUS- FOR HOTMELTEXTRUSION, in Google Patents, U. PTO, Editor. 1968, Barmer Maschinenfabrik Aktiengesellschaft Wuppertal-Oberbarmen, Germany.
11. McGinity, J. W. and F. Zhang, Hot-melt extrudable pharmaceutical formulation in Google Patents, U. PTO, Editor. 2002, University of Texas System: USA.
12. Miller, D. A., et al., STABILIZED HME COMPOSITION WITH SMALL DRUG PARTICLES, in Google Patents. 2008, BOARD OF REGENTS, THE UNIVERSITY OF TEXAS SYSTEM, Austin, TX (US): USA.
13. Alderman, D. A. and T. D. Wolford, Sustained release dosage form based on highly plasticized cellulose ether gels, in Google Patents. 1987, The Dow Chemical Company: USA.
14. Brough, C., et al., THERMO-KINETIC MIXING FOR PHARMACEUTICAL APPLICATIONS, in Google Patents. 2009, BOARD OF REGENTS, THE UNIVERSITY OF TEXAS SYSTEM, Austin, TX (US): USA.
15. Fischer, G., et al., MATRIX COMPOSITIONS FOR CONTROLLED DELIVERY OF DRUG SUBSTANCES, in Google Patents. 2007, EGALET A/S, Vaerlose (Denmark): USA.
16. Yang, R. K., et al., UNIFORM FILMS FOR RAPID DISSOLVE DOSAGE FORM INCORPORATING TASTE-MASKING COMPOSITIONS, in Google Patents. 2008, MONOSOLRX LLC, Portage, IN (US): USA.
17. Fuisz, R. C., et al., POLYMER-BASED FILMS AND DRUG DELIVERY SYSTEMS MADE THEREFROM, in Google Patents. 2007: USA.
18. Bernstein, H., et al., MATRICES FORMED OF POLYMER AND HYDROPHOBIC COMPOUNDS FOR USE IN DRUG DELIVERY, in Google Patents, U. PTO, Editor. 2004, Acusphere, Inc., Cambridge, MA (US): USA.
19. MacAllister, S. M., et al., Pharmaceutical Formulation, in Google Patents. 2004, SMITHKLINE BEECHAM CORPORATION.
20. McAllister, S. M., et al., PHARMACEUTICAL FORMULATION, in Google Patents. 2003, GLAXOSMITHKLINE.
21. Davies, D. L., et al., *Recent advances in the discovery and preclinical testing of novel compounds for the prevention and/or treatment of alcohol use disorders.* Alcoholism: Clinical and Experimental Research, 2013. 37(1): p. 8-15.
22. Liang, J., et al., *Dihydromyricetin prevents fetal alcohol exposure-induced behavioral and physiological deficits: the roles of GABAA receptors in adolescence.* Neurochemical research, 2014. 39(6): p. 1147-1161.
23. Shen, Y., et al., *Dihydromyricetin as a novel anti-alcohol intoxication medication.* Journal of Neuroscience, 2012. 32(1): p. 390-401.
24. Ji, Y., J. Li, and P. Yang, *Effects of fruits of Hovenia dulcis Thunb on acute alcohol toxicity in mice.* Zhong yao cai=Zhongyaocai=Journal of Chinese medicinal materials, 2001. 24(2): p. 126-128.
25. Fang, H.-L., et al., *Treatment of chronic liver injuries in mice by oral administration of ethanolic extract of the fruit of Hovenia dulcis.* The American journal of Chinese medicine, 2007. 35(04): p. 693-703.
26. Hase, K., et al., *Hepatoprotective Effect of Hovenia dulcis THUNB. on Experimental Liver Injuries Induced by Carbon Tetrachloride or D-Galactosamine: Lipopolysaccharide.* Biological and pharmaceutical Bulletin, 1997. 20(4): p. 381-385.
27. Ji, Y., et al., *Effects of Hovenia dulcis Thunb on blood sugar and hepatic glycogen in diabetic mice.* Zhong yao cai=Zhongyaocai=Journal of Chinese medicinal materials, 2002. 25(3): p. 190-191.
28. Okuma, Y., et al., *Effect of extracts from Hovenia dulcis Thunb. alcohol concentration in rats and men administered alcohol.* Journal of Japanese Society of Nutrition and Food Science (Japan), 1995.
29. WANG, X.-y. and Z.-t. JIANG, *RESEARCH PROGRESS IN NATURAL ANTIOXIDANT DIHYDROMYRICETIN* [J]. Food Research and Development, 2007. 2: p. 056.
30. Zhang, X., et al., *Scavenging effect of dihydromyricetin on the free radicals by ESR.* Modern Food Science and Technology, 2010. 26(10): p. 1040-1042, 1070.
31. Liu, B., et al., *Characterization and antioxidant activity of dihydromyricetin-lecithin complex.* European Food Research and Technology, 2009. 230(2): p. 325-331.
32. Aungst, B. J., *Absorption enhancers: applications and advances.* The AAPS journal, 2012. 14(1): p. 10-18.
33. Thanou, M., J. Verhoef, and H. Junginger, *Oral drug absorption enhancement by chitosan and its derivatives.* Advanced drug delivery reviews, 2001. 52(2): p. 117-126.

34. Whitehead, K., N. Karr, and S. Mitragotri, *Safe and effective permeation enhancers for oral drug delivery*. Pharmaceutical research, 2008. 25(8): p. 1782-1788.
35. Whitehead, K. and S. Mitragotri, *Mechanistic analysis of chemical permeation enhancers for oral drug delivery*. Pharmaceutical research, 2008. 25(6): p. 1412-1419.
36. Hu, J., K. P. Johnston, and R. O. Williams, *Nanoparticle Engineering Processes for Enhancing the Dissolution Rates of Poorly Water Soluble Drugs*. Drug development and industrial pharmacy, 2004. 30(3): p. 233-245.
37. Zhang, Y., et al., *Design and Solidification of Fast-Releasing Clofazimine Nanoparticles for Treatment of Cryptosporidiosis*. Molecular pharmaceutics, 2017. 14(10): p. 3480-3488.
38. Onoue, S., et al., *Self-micellizing solid dispersion of cyclosporine A with improved dissolution and oral bioavailability*. Eur J Pharm Sci, 2014. 62: p. 16-22.

The invention claimed is:

1. A dihydromyricetin (DHM) formulation, comprising:
   dihydromyricetin (DHM); and
   a matrix material,
   wherein the matrix material comprises poly(vinyl pyrrolidone-co-vinyl acetate) (PVP-VA),
   wherein the DHM is dissolved in the matrix material, and
   wherein the DHM formulation is homogeneous.

2. The DHM formulation of claim 1, wherein the matrix material further comprises a polymer selected from the group consisting of hydroxypropyl methyl cellulose (HPMC), cellulose ester, cellulose acrylate, methyl cellulose, ethyl cellulose, hydroxyethyl cellulose, hydroxypropylcellulose (HPC), hydroxypropyl methylcellulose propionate succinate, hydroxypropyl methyl cellulose phthalate (HPMCP), hydroxypropyl methyl cellulose acetate succinate (HPMCAS), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), carboxymethylcellulose, carboxymethylcellulose salt, sodium carboxymethylcellulose, a cellulose polymer, and combinations thereof.

3. The DHM formulation of claim 1, wherein the matrix material further comprises a polymer selected from the group consisting of polyethylene oxide (PEO), a polyoxyethylene-polyoxypropylene block copolymer (a poloxamer), a polyoxyethylene alkyl ether, a polyoxyethylene castor oil, an oligomer of polyethylene glycol, an ethylene glycol-vinyl glycol copolymer, a polyoxyethylene castor oil, an ethoxylated castor oil, a polyoxyl hydrogenated castor oil, a polyoxyl 40 hydrogenated castor oil, a polyethoxylated sorbitan, polyoxyethylene sorbitan monooleate, and combinations thereof.

4. The DHM formulation of claim 1, wherein the matrix material further comprises a polymer selected from the group consisting of poly(methyl methacrylate) (PMMA), polymethacrylate, methacrylic acid copolymers, a polymethacrylate derivative, poly(methacrylic acid-co-methyl methacrylate) 1:1, poly(methacrylic acid-co-methyl methacrylate) 1:2, poly(methacrylic acid-co-ethyl acrylate) 1:1, polycaprolactam, polycaprolactone (PCL), polylactic acid (PLA), polyglycolic acid (PGA), poly(lactic-glycolic acid) (PLGA), polyvinyl pyrrolidone (PVP), and combinations thereof.

5. The DHM formulation of claim 1, wherein the matrix material further comprises a material selected from the group consisting of a wax, carnauba wax, starch, a starch derivative, a sugar, a sugar alcohol, leucine, a lipid, a polyol, a polyether, fructose, glucose, lactose, mannitol, trehalose, sucrose, raffinose, maltitol, lactitol, sorbitol, xylitol, erythritol, xylose, acarbose, melezitose, galactose, melibrose, isomaltose, a natural sugar extract, malt beet sugar, corn sugar, high-fructose corn syrup, a sugar oligomer, polydextrose with molecular weight less than 10,000 Daltons, a dextran with molecular weight less than 10,000 Daltons, a polyol, glycerol, sorbitol, ethylene glycol, propylene glycol, butanediol, a polymeric derivative of vitamin E, poly(propylene), and combinations thereof.

6. The DHM formulation of claim 1, further comprising a plasticizer selected from the group consisting of triacetin, citrate ester, triethyl citrate, acetyl triethyl citrate, tributyl citrate, a polyol having aliphatic hydroxyls, poly(propylene glycol), poly(ethylene oxide) having an average molecular weight of less than about 500,000 Da, D-alpha tocopheryl PEG 1000 succinate (TPGS), polyethylene glycol, propylene glycol, 1,2-butylene glycol, 2,3-butylene glycol, triethylene glycol, tetraethylene glycol, mono propylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, allyl glycolate, vitamin E, pressurized $CO_2$, and combinations thereof.

7. The DHM formulation of claim 1, further comprising a permeabilizer selected from the group consisting of caprylic acid, a caprylate salt, sodium caprylate, and combinations thereof.

8. The DHM formulation of claim 1, further comprising a permeabilizer selected from the group consisting of a fatty acid, a saturated fatty acid, a fatty acid complexed with a cation, a fatty acid complexed with a metal cation, a metal divalent cation, a magnesium divalent cation, a calcium divalent cation, a zinc divalent cation, an iron divalent cation, a metal trivalent cation, and/or an iron trivalent cation, a fatty acid salt, a fatty acid metallic soap, and combinations thereof.

9. The DHM formulation of claim 1, further comprising a coactive selected from the group consisting of L-cysteine, N-acetyl cysteine (NAC), Prickly Pear extract, Milk Thistle, ginger root, vitamin B, an antioxidant, glutathione, vitamin C, vitamin E, an electrolyte, a sugar, and combinations thereof.

10. The DHM formulation of claim 1, further comprising a pH buffering agent selected from the group consisting of an acidic pH buffering agent, citric acid, a citrate salt, a sodium citrate, a potassium citrate, calcium citrate, and combinations thereof.

11. The DHM formulation of claim 1,
    wherein the DHM is not solubilized or dissolved by an aqueous solution having a pH of at most 3.5 and
    wherein the DHM is solubilized or dissolved by an aqueous solution having a pH of at least 5.5.

12. The DHM formulation of claim 1,
    wherein the DHM comprises at least 20 wt % of the formulation.

13. A dosage form, comprising
    the DHM formulation of claim 1; and
    an enteric coating that encapsulates the DHM formulation, wherein the enteric coating is selected from the group consisting of a polymeric coating and a methacrylate copolymer coating.

14. A dosage form, comprising
the DHM formulation of claim 1 in a powder form; and
an aqueous liquid or a gel,
wherein the DHM formulation in a powder form is mixed with or suspended in the aqueous liquid or the gel.

15. The DHM formulation of claim 1,
wherein the matrix material is poly(vinyl pyrrolidone-co-vinyl acetate) (PVP-VA) and
wherein the DHM comprises at least 20 wt % of the DHM formulation.

16. A method for forming the dihydromyricetin (DHM) formulation of claim 1, comprising:
mixing the dihydromyricetin (DHM) and the matrix material to form a compounding mixture;
processing the compounding mixture in an extruder to form an extrudate; and
collecting the extrudate as the dihydromyricetin (DHM) formulation.

17. The method of claim 16, wherein an operating temperature of the extruder is less than a melting temperature of the dihydromyricetin (DHM).

18. A method for reducing hangover symptoms, comprising
administering the dihydromyricetin (DHM) formulation of claim 1 to a patient suffering from hangover symptoms,
so that the patient's hangover symptoms are reduced.

19. The dihydromyricetin (DHM) formulation of claim 1 for use in preventing an alcohol use disorder or preventing alcoholism.

20. The dihydromyricetin (DHM) formulation of claim 1 for use in treating an alcohol use disorder, treating alcoholism, or treating an alcohol overdose.

21. The dihydromyricetin (DHM) formulation of claim 1 for use in increasing antioxidant capacity, neuroprotection, treating Alzheimer's disease, or inhibiting inflammation.

22. The dihydromyricetin (DHM) formulation of claim 1 for use in protecting the kidney or protecting the liver.

23. The dihydromyricetin (DHM) formulation of claim 1 for use in treating cancer.

24. The dihydromyricetin (DHM) formulation of claim 1 for use in ameliorating a metabolic disorder or treating diabetes.

25. The dihydromyricetin (DHM) formulation of claim 1 for use in treating a bacterial infection.

* * * * *